United States Patent
Band et al.

(10) Patent No.: US 9,939,450 B2
(45) Date of Patent: *Apr. 10, 2018

(54) QUANTIFYING LOCAL INFLAMMATORY ACTIVITY AND ITS USE TO PREDICT DISEASE PROGRESSION AND TAILOR TREATMENTS

(71) Applicants: New York University, New York, NY (US); Duke University Medical Center, Durham, NC (US)

(72) Inventors: Philip A. Band, West Orange, NJ (US); Hans-Georg Wisniewski, Riverdale, NY (US); Virginia Byers Kraus, Hillsborough, NC (US)

(73) Assignees: New York University, New York, NY (US); Duke University Medical Center, Durham, NC (US)

( * ) Notice: Subject to any disclaimer, the term of this patent is extended or adjusted under 35 U.S.C. 154(b) by 240 days.

This patent is subject to a terminal disclaimer.

(21) Appl. No.: 14/537,732

(22) Filed: Nov. 10, 2014

(65) Prior Publication Data
US 2015/0204888 A1     Jul. 23, 2015

Related U.S. Application Data

(63) Continuation of application No. 13/172,300, filed on Jun. 29, 2011, now Pat. No. 8,883,427.

(60) Provisional application No. 61/360,323, filed on Jun. 30, 2010.

(51) Int. Cl.
*G01N 33/68* (2006.01)

(52) U.S. Cl.
CPC . *G01N 33/6893* (2013.01); *G01N 2333/4703* (2013.01); *G01N 2333/811* (2013.01); *G01N 2400/40* (2013.01); *G01N 2800/105* (2013.01); *G01N 2800/56* (2013.01); *G01N 2800/7095* (2013.01)

(58) Field of Classification Search
CPC ..... G01N 2333/4703; G01N 2333/811; G01N 2400/40; G01N 2800/105; G01N 2800/56; G01N 2800/7095; G01N 33/6893
See application file for complete search history.

(56) References Cited

U.S. PATENT DOCUMENTS

| 8,883,427 B2 * | 11/2014 | Band | G01N 33/6893 435/7.1 |
|---|---|---|---|
| 2008/0131439 A1 | 6/2008 | Lois et al. | |
| 2009/0221904 A1 | 9/2009 | Shealy et al. | |
| 2009/0270272 A1 | 10/2009 | Karl et al. | |
| 2009/0311707 A1 | 12/2009 | Xia | |

OTHER PUBLICATIONS

Yoshihara et al., "Superficial Zone Chondrocytes in Normal and Osteoarthritic Human Articular Cartilages Synthesize Novel Truncated Forms of Inter-Alpha-Trypsin Inhibitor Heavy Chains which are Attached to a Chondroitin Sulfate Proteoglycan Other than Bikunin," Osteoarthritis and Cartilage 16:1343-1355 (2008).
Valdes et al., "Association Study of Candidate Genes for the Prevalence and Progression of Knee Osteoarthritis," Arthritis & Rheumatism 50(8):2497-2507 (2004).
Filkova et al., "Serum Hyaluronic Acid as a Potential Marker with a Predictive Value for Further Radiographic Progression of Hand Osteoarthritis," Osteoarthritis and Cartilage 17:1615-1619 (2009).
Jessen et al., "TSG-6 and Calcium Ions are Essential for the Coupling of Inter-Alpha-Trypsin Inhibitor to Hyaluronan in Human Synovial Fluid," Osteoarthritis and Cartilage 12:142-148 (2004).
Bayliss et al., "Up-Regulation and Differential Expression of the Hyaluronan-Binding Protein TSG-6 in Cartilage and Synovium in Rheumatoid Arthritis and Osteoarthritis," Osteoarthritis and Cartilage 9:42-48 (2001).
Colon et al., "Transfer of Inter-alpha-Inhibitor Heavy Chains to Hyaluronan by Surface-Linked Hyaluronan-TSG-6 Complexes," J. Biol. Chem. 284(4):2320-2331 (2009).
Rugg et al., "Characterization of Complexes Formed between TSG-6 and Inter-alpha-Inhibitor that Act as Intermediates in the Covalent Transfer of Heavy Chains onto Hyaluronan," J. Biol. Chem. 280(27):25674-25686 (2005).
International Search Report for International Patent Application No. PCT/US2011/042394 (dated Feb. 29, 2012).
Written Opinion of the International Searching Authority for International Patent Application No. PCT/US2011/042394 (dated Feb. 29, 2012).
Ellegaard et al., "Ultrasound Colour Doppler Measurements in a Single Joint as Measure of Disease Activity in Patients with Rheumatoid Arthritis-Assessment of Concurrent Validity," Rheumatology 48:254-257 (2009).

(Continued)

*Primary Examiner* — Galina Yakovleva
(74) *Attorney, Agent, or Firm* — LeClairRyan, a Professional Corporation

(57) ABSTRACT

This invention relates to a method of predicting progression of an inflammatory condition in a subject, which involves providing a medium comprising hyaluronan or a fragment thereof; contacting the medium with a fluid sample from a subject with an inflammatory condition, where the fluid sample comprises proteins or proteoglycans and a transfer agent; incubating the fluid sample with the medium under conditions effective for the transfer agent in the fluid sample to mediate transfer of heavy chains from the proteins or proteoglycans to the hyaluronan or a fragment thereof to form a complex; detecting, using an antibody, occurrence levels of the complex; and comparing occurrence levels of the complex from said detecting to a reference standard to predict progression of an inflammatory condition in the subject. Also disclosed are methods of tailoring treatment of an inflammatory condition and quantifying local inflammatory activity in a body fluid.

8 Claims, 12 Drawing Sheets

(56) References Cited

OTHER PUBLICATIONS

Milner et al., "TSG-6: A Multifunctional Protein Associated with Inflammation," J. Cell Sci. 116:1863-1873 (2003).

Wisniewski et al., "TSG-6: A TNF-, IL-1, and LPS-Inducible Secreted Glycoprotein Associated with Arthritis," J. Immunol. 151(11):6593-6601 (1993).

Pavelka et al., "Hyaluronic Acid Levels may have Predictive Value for the Progression of Knee Osteoarthritis," Osteoarthritis and Cartilage 12(4):277-283 (2004).

Dixey et al., "Is it Possible to Predict Radiological Damage in Early Rheumatoid Arthritis (RA)? A Report on the Occurrence, Progression, and Prognostic Factors of Radiological Erosions Over the First 3 Years in 866 Patients from the Early RA Study (ERAS)," J. Rheumatol. 31(Suppl. 69):48-54 (2004).

* cited by examiner 03-12-10 SFs RANKED .JMP

| ROWS | SYNOVIAL FLUID | TSG-6 ACTIVITY (nM) | TSG-6 SCORE (WB) | OUTCOME |
| --- | --- | --- | --- | --- |
| 1 | 346 L | 2.3 | 0 | non-prog |
| 2 | 145 L | 3.3 | 0 | OST+ |
| 3 | 157 R | 3.4 | 1 | non-prog |
| 4 | 147 R | 4 | 0 | non-prog |
| 5 | 132 L | 4.2 | 1 | OST+ |
| 6 | 147 L | 4.2 | 1 | non-prog |
| 7 | 256 R | 4.2 | 0 | non-prog |
| 8 | 314 L | 4.3 | 0 | non-prog |
| 9 | 168 L | 4.5 | 0 | OST+ |
| 10 | 185 R | 4.7 | 0 | OST+ |
| 11 | 134 L | 5 | 0 | OST+ |
| 12 | 254 R | 5 | 0 | OST+ |
| 13 | 208 L | 5.3 | 0 | OST+ |
| 14 | 218 L | 5.4 | 3 | non-prog |
| 15 | 169 R | 5.6 | 0 | OST+ |
| 16 | 202 R | 5.7 | 0 | non-prog |
| 17 | 330 L | 5.7 | 0 | non-prog |
| 18 | 168 R | 5.9 | 0 | OST+ |
| 19 | 143 L | 6.2 | 0 | OST+ |
| 20 | 150 L | 6.2 | 0 | OST+ |
| 21 | 254 L | 6.5 | 0 | non-prog |
| 22 | 140 L | 6.7 | 2 | non-prog |
| 23 | 223 L | 6.9 | 3 | JSN+ |
| 24 | 184 R | 7.1 | 0 | OST+ |
| 25 | 293 R | 7.4 | 0 | non-prog |
| 26 | 261 L | 7.9 | 0 | JSN+ |
| 27 | 306 R | 7.9 | 0 | non-prog |
| 28 | 279 L | 8.4 | 0 | OST+ |
| 29 | 283 R | 8.4 | 0 | non-prog |
| 30 | 198 L | 8.5 | 0 | OST+ |
| 31 | 175 L | 8.7 | 3 | OST+ |

*FIG. 7A*

| ROWS | SYNOVIAL FLUID | TSG-6 ACTIVITY (nM) | TSG-6 SCORE (WB) | OUTCOME |
| --- | --- | --- | --- | --- |
| 32 | 201 L | 8.8 | 0 | non-prog |
| 33 | 159 R | 9 | 0 | JSN+ |
| 34 | 140 R | 9.1 | 1 | OST+ |
| 35 | 269 R | 9.3 | 0 | TKR |
| 36 | 279 R | 9.5 | 0 | OST+ |
| 37 | 203 R | 9.6 | 1 | non-prog |
| 38 | 296 R | 10 | 0 | non-prog |
| 39 | 217 R | 10.2 | 0 | OST+ |
| 40 | 181 L | 10.4 | 0 | OST+ |
| 41 | 261 R | 10.4 | 0 | non-prog |
| 42 | 239 R | 11 | 0 | non-prog |
| 43 | 179 L | 11.8 | 1 | JSN+ |
| 44 | 196 L | 11.9 | 0 | OST+ |
| 45 | 248 L | 12.3 | 0 | non-prog |
| 46 | 142 R | 12.5 | 0 | OST+ |
| 47 | 283 L | 13.1 | 0 | OST+ |
| 48 | 143 R | 13.3 | 2 | TKR |
| 49 | 196 R | 13.5 | 1 | OST+ |
| 50 | 198 R | 13.7 | 1 | TKR |
| 51 | 181 R | 14.1 | 0 | JSN+ |
| 52 | 299 R | 14.6 | 1 | non-prog |
| 53 | 315 R | 14.8 | 1 | non-prog |
| 54 | 284 R | 15.5 | 0 | TKR |
| 55 | 315 L | 15.8 | 1 | OST+ |
| 56 | 236 L | 16.7 | 1 | JSN+ |
| 57 | 178 L | 17.2 | 1 | JSN+ |
| 58 | 214 L | 17.7 | 2 | OST+ |
| 59 | 269 L | 17.8 | 1 | JSN+ |
| 60 | 228 R | 19.9 | 2 | non-prog |
| 61 | 172 R | 21.4 | 1 | TKR |
| 62 | 219 R | 28 | 3 | TKR |
| 63 | 175 R | 29.4 | 3 | OST+ |
| 64 | 154 R | 30.4 | 3 | TKR |
| 65 | 221 L | 49.6 | 3 | TKR |

*FIG. 7B*

LOGISTIC REGRESSION CONTROLLING FOR AGE, GENDER, BMI, BASELINE PAIN, AND BASELINE KL GRADE

| PRIMARY OUTCOME MEASURE | ODDS RATIO (95% CI) | P-VALUE |
|---|---|---|
| TKR | 1.22 (1.07 - 1.41) | 0.003* |
| JSN+ (OST+) | 1.23 (1.01 - 1.47) | 0.017* |
| OST+ (JSN-) | --- | 0.848 |

* ODDS RATIO SIGNIFICANTLY DIFFERENT FROM 1

EACH UNIT INCREASE IN TSG-6 ACTIVITY (I.E., 1nM) IS ASSOCIATED WITH A 22% INCREASE IN THE ODDS OF TKA WITHIN 3 YEARS

*FIG. 10*

QUANTIFYING LOCAL INFLAMMATORY ACTIVITY AND ITS USE TO PREDICT DISEASE PROGRESSION AND TAILOR TREATMENTS

This application is a continuation of U.S. patent application Ser. No. 13/172,300, filed Jun. 29, 2011, which claims the benefit of U.S. Provisional Patent Application Ser. No. 61/360,323, filed Jun. 30, 2010, each of which are hereby incorporated by reference in their entirety.

FIELD OF THE INVENTION

This invention relates to methods of quantifying local inflammatory activity and its use to predict disease progression and tailor treatments.

BACKGROUND OF THE INVENTION

Osteoarthritis ("OA") of the knee presents a current and growing challenge to the available orthopaedic resources in the United States. At the present time, OA is one of the leading causes of chronic disability, with recent estimates reporting that symptomatic knee OA occurs in 13% of people age 60 years and older (Bauer et al., "Classification of Osteoarthritis Biomarkers: A Proposed Approach," *Osteoarthritis Cartilage* 14(8):723-7 (2006); Lawrence et al., "Estimates of the Prevalence of Arthritis and Selected Musculoskeletal Disorders In the United States," *Arthritis Rheum.* 41(5):778-99 (1998)). Between 2000 and 2010, the number of total knee replacements ("TKR") in the U.S. doubled, and is anticipated to approach 3.8 million cases per year by 2030 (Kurtz et al., "Projections of Primary and Revision Hip and Knee Arthroplasty In the United States From 2005 to 2030," *J. Bone Joint Surg. Am.* 89:780-5 (2007)). Moreover, during the past decade the average age of patients undergoing TKR decreased from 66 to 57 years of age, a troubling trend considering the surgical difficulty and cost associated with revision arthroplasty. With the anticipated increase in disease prevalence and its associated drain on health care resources, there is a clear and pressing need to develop improved decision models with respect to the treatment of knee OA including the appropriate timing of TKR and evidence-based guidelines to indicate when the utilization of treatment alternatives is indicated.

Osteoarthritis is a complex, multifactorial disease of uncertain etiology. Current hypotheses focus on a combination of endogenous factors such as age, sex, and genetics with important contributions from exogenous factors such as repetitive weightbearing loads and traumatic events (Lohmander and Felson, "Can We Identify a 'High Risk' Patient Profile to Determine Who Will Experience Rapid Progression of Osteoarthritis," *Osteoarthritis Cartilage* 12 Suppl. A:S49-52 (2004)). Both clinical and basic science research is presently focused not only on identifying the factors that initiate OA, but also those that contribute to its progression. While the natural history of knee OA is not clearly understood, there is data to suggest that the rate of progression of the disease is variable. This phenomenon may reflect a differential local production of inflammatory cytokines by patients based on their genetic background and the sensitivity of their innate immune system. The ability to categorize patients with symptomatic OA according to their predicted rate of disease progression would have a significant impact on decision making with respect to the recommended course of treatment, including the appropriate timing of TKR.

Biomarkers are defined as objective indicators of normal biologic processes, pathologic processes, or pharmacologic responses to therapeutic interventions (Bauer et al., "Classification of Osteoarthritis Biomarkers: A Proposed Approach," *Osteoarthritis Cartilage* 14(8):723-7 (2006); De Gruttola et al., "Considerations In the Evaluation of Surrogate Endpoints In Clinical Trials. Summary of a National Institutes of Health Workshop," *Control Clin. Trials* 22(5): 485-502 (2001)). During the last 10 years, significant progress has been made toward developing biomarkers for osteoarthritis. For example, Sharif et al., "Suggestion of Nonlinear or Phasic Progression of Knee Osteoarthritis Based On Measurements of Serum Cartilage Oligomeric Matrix Protein Levels Over Five Years," *Arthritis Rheum.* 50(8):2479-88 (2004), recently demonstrated that mean serum levels of the biomarker cartilage oligmeric matrix protein ("COMP") was related to progressive joint damage in cases of knee OA. In their study of 115 patients, the authors reported that serum COMP levels were significantly higher amongst patients with progressive disease compared to those with quiescent disease and that on average, a one unit increase in COMP level corresponded to a 15% probability of radiographic progression over a 6 month period. In a cohort of 377 patients with symptomatic knee OA, Garnero et al., "Bone Marrow Abnormalities On Magnetic Resonance Imaging are Associated With Type II Collagen Degradation In Knee Osteoarthritis: A Three-month Longitudinal Study," *Arthritis Rheum.* 52(9):2822-9 (2005), reported that MRI evidence of worsening OA-related bone marrow abnormalities could be predicted based on the urinary excretion of C-terminal crosslinking telopeptide of type II collagen ("CTX-II"). In that study, patients with baseline urinary CTX-II levels in the highest tertile had a relative risk of 2.4 of worsening bone marrow abnormalities at 3 months compared with patients with levels in the lowest tertile.

For a variety of disease states the use of biomarkers has been advantageous as a part of the diagnostic workup, helping to customize therapy for distinct patient subgroups. At the present time, the preponderance of research on the use of biomarkers has been performed using blood and urine as sample sources secondary to their ready availability. While a number of recent studies have investigated changes in synovial fluid characteristics during the OA disease process (see, e.g., Gandhi et al., "The Synovial Fluid Adiponectin-leptin Ratio Predicts Pain With Knee Osteoarthritis," *Clin. Rheumatol.*, Mar. 28, 2010; Gao et al., "Elevated Osteopontin Level of Synovial Fluid and Articular Cartilage Is Associated With Disease Severity In Knee Osteoarthritis Patients," *Osteoarthritis Cartilage* 18(1):82-7 (2010); Hao et al., "Synovial Fluid Level of Adiponectin Correlated With Levels of Aggrecan Degradation Markers In Osteoarthritis," *Rheumatol. Int.*, May 13, 2010; Neu et al., "Friction Coefficient and Superficial Zone Protein Are Increased In Patients With Advanced Osteoarthritis," *Arthritis Rheum.*, May 24, 3010; Sutipornpalangkul et al., "Lipid Peroxidation, Glutathione, Vitamin E, and Antioxidant Enzymes In Synovial Fluid from Patients With Osteoarthritis," *Int. J. Rheum. Dis.* 12(4):324-8 (2009)), no data is available regarding the utility of synovial fluid biomarkers to distinguish OA subgroups, particularly as these relate to treatment recommendations and the risk of progression to severe degenerative joint disease and total knee replacement.

One reason for the limited availability of synovial fluid biomarker data is the difficulty of collecting and analyzing synovial fluid from arthritic knees that do not present with an effusion, the so-called "dry joint." Recently, closed-needle lavage procedures have been developed which enable the standardized collection of synovial fluid for quantitative biomarker analysis (FIG. 12). Closed-needle lavage is a safe, office-based procedure which in addition to enabling the acquisition of synovial fluid for analysis has been shown to provide significant symptomatic benefit for some patients with knee OA (Chang et al., "A Randomized, Controlled Trial of Arthroscopic Surgery Versus Closed-needle Joint Lavage for Patients With Osteoarthritis of the Knee," *Arthritis Rheum.* 36(3):289-96 (1993); Ike et al., "Tidal Irrigation Versus Conservative Medical Management In Patients With Osteoarthritis of the Knee: A Prospective Randomized Study. Tidal Irrigation Cooperating Group," *J. Rheumatol.* 19(5):772-9 (1992)). In a prospective randomized trial of closed-needle lavage compared to conservative medical management in 77 patients with knee OA, Ike et al., "Tidal Irrigation Versus Conservative Medical Management In Patients With Osteoarthritis of the Knee: A Prospective Randomized Study. Tidal Irrigation Cooperating Group," *J. Rheumatol.* 19(5):772-9 (1992), demonstrated significant differences favoring lavage with respect to pain after a 50 foot walk, pain after a 4 stair climb, frequency of knee stiffness, and overall assessment of therapy effectiveness.

There is a need for highly sensitive, specific, and quantitative assays for the determination of biomarkers that represent an overall summation of local inflammatory conditions in patient specimens. While assays for some biomarkers of inflammation are available for research purposes, these measure the quantity of the specific biomarker present, and do not provide an integrated measure of the cytokine-induced inflammatory activity present in a biological specimen.

The present invention is directed to overcoming these and other limitations in the art.

SUMMARY OF THE INVENTION

One aspect of the present invention is directed to a method of predicting progression of an inflammatory condition in a subject. This method involves providing a medium comprising hyaluronan or a fragment thereof. The medium is contacted with a fluid sample from a subject with an inflammatory condition. The fluid sample comprises proteins or proteoglycans and a transfer agent. The fluid sample is incubated with the medium under conditions effective for the transfer agent in the fluid sample to mediate transfer of heavy chains from the proteins or proteoglycans to the hyaluronan or a fragment thereof to form a complex. Using an antibody, occurrence levels of the complex are detected. Occurrence levels of the complex from said detecting are compared to a reference standard to predict progression of an inflammatory condition in the subject.

Another aspect of the present invention is directed to a method of tailoring treatment of an inflammatory condition in a subject in need of treatment. This method involves providing a medium comprising hyaluronan or a fragment thereof. The medium is contacted with a fluid sample from a subject with an inflammatory condition. The fluid sample comprises proteins or proteoglycans and a transfer agent. The fluid sample is incubated with the medium under conditions effective for the transfer agent in the fluid sample to mediate transfer of heavy chains from the proteins or proteoglycans to the hyaluronan or a fragment thereof to form a complex. Occurrence levels of the complex are detected using an antibody. Occurrence levels of the complex from said detecting are compared to a reference standard to predict progression of an inflammatory condition in the subject. The method further involves determining treatment of the inflammatory condition in the subject based on said comparing, thereby tailoring treatment of the inflammatory condition in the subject.

A further aspect of the present invention is directed to a method of quantifying local inflammatory activity in a body fluid. This method involves providing a medium comprising hyaluronan or a fragment thereof. The medium is contacted with a fluid sample from a subject with an inflammatory condition. The fluid sample comprises proteins or proteoglycans and a transfer agent. The fluid sample is incubated with the medium under conditions effective for the transfer agent in the fluid sample to mediate transfer of heavy chains from the proteins or proteoglycans to the hyaluronan or a fragment thereof to form a complex. Occurrence levels of the complex are detected using an antibody. Occurrence levels of the complex from said detecting are compared to a reference standard to quantify local inflammatory activity in a body fluid.

According to the present invention, synovial fluid biomarkers detected as transfer activity are significantly associated with the risk of radiographic and clinical OA progression. Accordingly, methods of the present invention employ biomarkers that can be incorporated into decision models for determining the timing of TKR (and other joint surgeries) and utilization of available treatment alternatives.

According to one embodiment of the present invention, TNF-stimulated gene 6 protein ("TSG-6") levels in synovial fluid of subjects with osteoarthritis, as determined by immunological methods such as immunoblotting or ELISA, are significantly predictive of the risk of osteroarthritis progression, with progression defined over a 3-year period, based on progressive joint space narrowing, osteophyte formation (progressive radiographic changes), or progression to total knee replacement surgery. Based on the catalytic property of TSG-6 for this transfer activity, a quantitative, sensitive, and specific assay has been developed for the determination of transfer activity in body fluids (e.g., synovial fluid, serum, plasma, etc.), whether or not the transfer activity results specifically from the TSG-6 content in the body fluid of interest. This TSG-6 activity assay can be conducted in certain body fluids (e.g., synovial fluid, blood, amniotic fluid, etc.) without the addition of exogenous inter α inhibitor ("IαI"), which can serve as the donor of HC, because the level of IαI in the body fluid is likewise controlled by inflammatory processes such as extravasation and edema. The transfer activity determined by this assay may be dependent on, in addition to the presence of TSG-6 protein or any other protein or proteoglycan that can catalyze this transfer, the concentration of IαI, the concentration of hyaluronic acid ("HA"), the molecular weight distribution of HA, and the modification of HA by associated heavy chains ("HCs") in the specimen. Therefore, the assay may be not only a determinant of TSG-6 protein, but an integrated measure of multiple factors whose presence in the sample is modulated by local inflammation, and also by systemic factors that affect vascular permeability and liver function.

The immediate application is to identify OA phenotype in individual patients, including individual risk factors and etiological factors, and to customize treatment to the individual patient's needs. Moreover, because this assay can be used to identify patients at high risk of progression, it is especially useful to identify patients that should be recruited into clinical trials of agents intended to modify disease progression, and can thereby dramatically reduce the number of patients that need to be recruited into such trials, reduce the cost of such trials, and increase their feasibility.

The assay can be used as a point-of-care diagnostic tool, thereby applying principles of personalized medicine to the care of osteoarthritis. Besides osteoarthritis, the assay can also be used for determination of TSG-6 in other pathologic conditions, e.g., in rheumatoid arthritis, fertility problems, and liver disease.

BRIEF DESCRIPTION OF THE DRAWINGS

FIGS. 7A-7B are a table providing a listing of OA patients ranked by transfer agent activity.

FIG. 10 is a table presenting the odds ratios for progression to end-stage OA requiring total knee replacement (TKR) or joint space narrowing (JSN) within three years after determination of the TSG-6 activity in the study cohort of OA patients. An odds ratio of 1.22 for progression to TKR means that an increase of the TSG-6 activity by one unit (i.e., 1 nM) is associated with a 22% increase of the odds of progression to TKR within three years.

FIG. 12 shows the difference in procedure for patients who present with a clinically detectable effusion (excess fluid in the joint) compared to patients from whom no fluid sample can be obtained (so-called "dry joints"). In "dry joint" patients, it is possible to introduce a small volume of solution (e.g., physiologic buffered saline) to flush biomarkers from the joint. The latter situation requires that a small blood sample also be obtained in order to calculate the dilution of the biomarker by the lavage fluid using the urea dilution method (Kraus et al., "Urea as a Passive Transport Marker for Arthritis Biomarker Studies," *Arthritis & Rheum.* 46(2):420-427 (2002.), which is hereby incorporated by reference in its entirety).

DETAILED DESCRIPTION OF THE INVENTION

Figure 1:
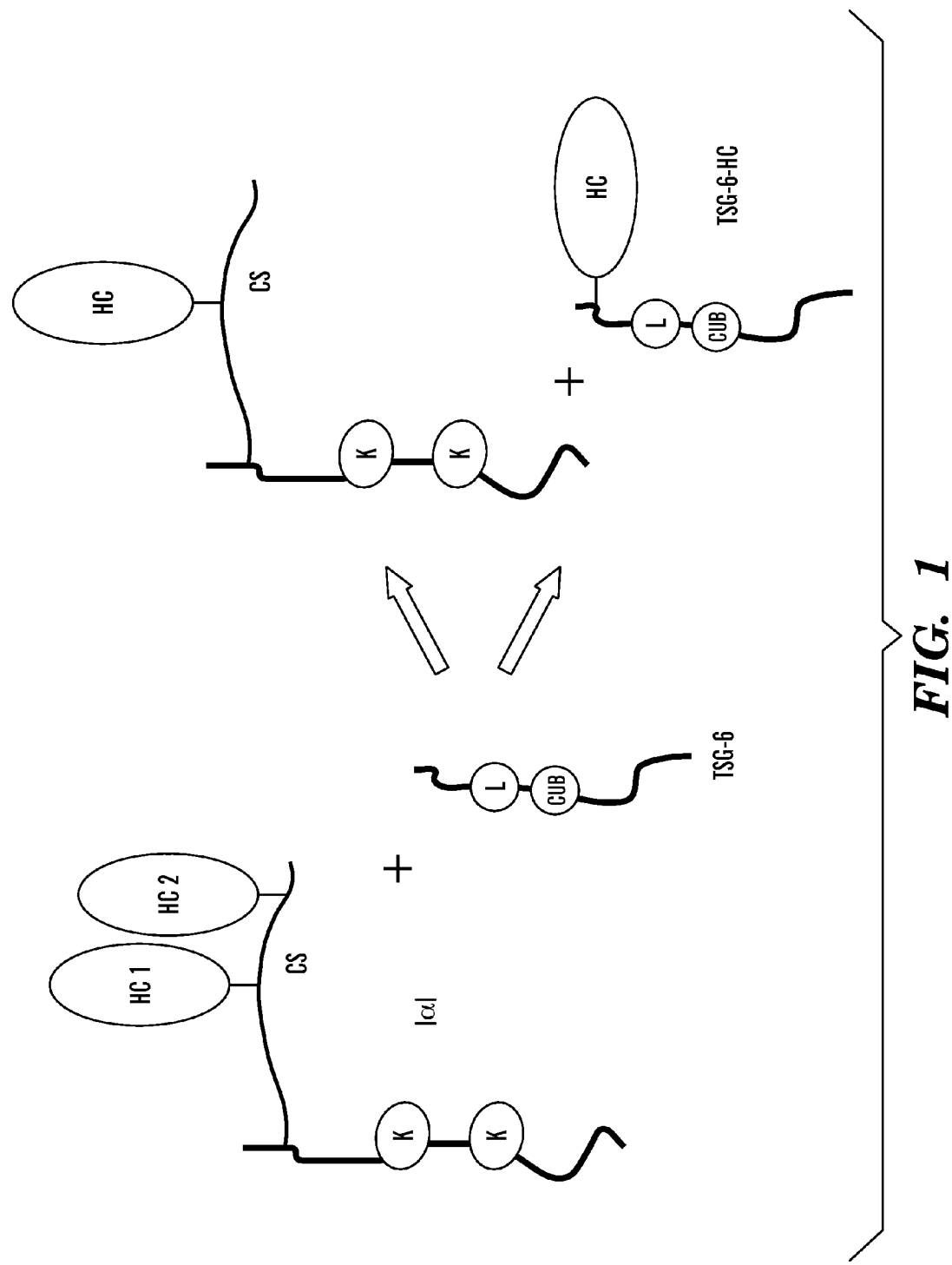
FIG. 1 is a schematic illustration of the principle of a TSG-6 activity assay according to one embodiment of the present invention. As illustrated, both TSG-6 and IαI are present in synovial fluid of patients with arthritis. The reaction depicted in FIG. 1 can proceed in synovial fluid at an elevated temperature (e.g., 37° C.) in the absence of added HA. Heavy chains (HC) are transferred from IαI to TSG-6, the resulting TSG-6-HC complexes are stable intermediates for the transfer to HA. K, the two homologous Kunitz domains of bikunin, the protease inhibitor component of IαI; CS, chondroitin-4-sulfate; L, link domain of TSG-6; CUB, CUB domain of TSG-6.

One aspect of the present invention is directed to a method of predicting progression of an inflammatory condition in a subject. This method involves providing a medium comprising hyaluronan or a fragment thereof. The medium is contacted with a fluid sample from a subject with an inflammatory condition. The fluid sample comprises proteins or proteoglycans and a transfer agent. The fluid sample is incubated with the medium under conditions effective for the transfer agent in the fluid sample to mediate transfer of heavy chains from the proteins or proteoglycans to the hyaluronan or a fragment thereof to form a complex. Using an antibody, occurrence levels of the complex are detected. Occurrence levels of the complex from said detecting are compared to a reference standard to predict progression of an inflammatory condition in the subject.

Hyaluronan (or hyaluronic acid) is a high molecular weight compound having a molecular weight of between 50,000 daltons and several million daltons. The average molecular weight in human synovial fluid is 3-4 million Da, and hyaluronan purified from a human umbilical cord is 3,140,000 Da (Saari et al., "Differential Effects of Reactive Oxygen Species On Native Synovial Fluid and Purified Human Umbilical Cord Hyaluronate," *Inflammation* 17:403-415 (1993), which is hereby incorporated by reference in its entirety). The basic building block of hyaluronic acid is an aminodisaccharide which includes D-glucuronic acid and N-acetyl-D-glucosamine which are linked by a β-1,3 glycosidic bond. This basic building block is linked to the next unit by a β-1,4 glycosidic bond. This unbranched hyaluronic acid chain consists of from about 2,000 to 10,000 of such basic units. Hyaluronidases hydrolyse the β-glucosidic bonds and the hyaluronic acid is in this way broken down into smaller fragments. According to the present invention, hyaluronic acid, or hyaluronic acid fragments, are contained in a medium (or, e.g., coupled to a support). Fragments may be created by isolating hyaluronic acid from natural sources and, e.g., comminuted mechanically by shearing forces and/or ultrasonication, after which the polysaccharides may be subjected to further degradation using a suitable hyaluronidase or hyaluronan lyase. Suitable fragments may be, e.g., from 20 to 20,000 disaccharide units. Fragments of this size can then be isolated using suitable separation methods. See, e.g., U.S. Pat. No. 6,838,086 to Simon et al., which is hereby incorporated by reference in its entirety. In one embodiment, the hyaluronan has a molecular weight of about 2,000,000 Da.

According to one embodiment, hyaluronic acid or its fragments are modified chemically to accommodate the particular medium in which they are contained (e.g., immobilization on a support). Examples of modifications may include esterification, salt formation, amidation, reduction of an acid group to the aldehyde or alcohol, or elimination of an acid group. Salts and esters of hyaluronic acid or hyaluronic acid fragments may include alkali metal salts and alkaline earth metal salts, and $C_1$-$C_{10}$-alkyl esters. Other chemical modifications are also possible and can be effected by a person of ordinary skill in the art.

In vertebrates, hyaluronan is a major structural element of the extracellular matrix and plays roles in adhesion and recognition. Hyaluronan has a high negative charge density and numerous hydroxyl groups. Therefore, the molecule assumes an extended and hydrated conformation in solution. The viscoelastic properties of cartilage and synovial fluid are, in part, the result of the physical properties of the hyaluronan polysaccharide.

Many biological factors, such as growth factors, cytokines, eicosanoids, and so on, are generated in the inflammation process. These factors are necessary for the subsequent steps of wound healing due to their roles in promoting migration of inflammatory cells, fibroblasts, and endothelial cells into the wound site. The wound tissue in the early inflammatory phase of wound repair is abounding with hyaluronan, probably a reflection of increased synthesis. Hyaluronan participates in the biological processes associated with early inflammation, which is crucial in tissue regeneration, healing processes, and the innate immune response. In a murine air pouch model of carrageenan/IL-1-induced inflammation, hyaluronan was observed to enhance cellular infiltration (Wisniewski et al., "TNF/IL-1-inducible Protein TSG-6 Potentiates Plasmin Inhibition By Inter-alpha-inhibitor and Exerts a Strong Anti-inflammatory Effect *In Vivo*," *The Journal of Immunology* 156:1609-1615 (1996); Wisniewski et al., "TSG-6, A Glycoprotein Associated With Arthritis, and Its Ligand Hyaluronan Exert Opposite Effects In a Murine Model of Inflammation," *Pflugers Arch.* 431:R225-6 (1996), which are hereby incorporated by reference in their entirety).

According to the methods of the present invention, a medium is provided comprising hyaluronan or a fragment thereof. Suitable mediums include solutions or a support structure. When a support is utilized, hyaluronan and/or a fragment thereof, is coupled to a surface of the support. Suitable supports include anything having a surface upon which it may be desirable to immobilize hyaluronan for carrying out one embodiment of the methods of the present invention. The support may be either organic or inorganic, biological or non-biological, or any combination thereof. The support can comprise a material selected from, for example, silicon, silica, quartz, glass, polymer, controlled pore glass, carbon, alumina, titania, tantalum oxide, germanium, silicon nitride, zeolites, cellulose, paper, and gallium arsenide. Many metals such as gold, platinum, aluminum, copper, titanium, and their alloys are also suitable materials for supports pursuant to the methods of the present invention. In addition, ceramics and polymers may also be used as supports. Polymers which may be used as support materials may include, without limitation, the following: polystyrene; poly(tetra)fluoroethylene (PTFE); polyvinylidenedifluoride; polycarbonate; polymethylmethacrylate; polyvinylethylene; polyethyleneimine; poly(etherether)ketone; polyoxymethylene (POM); polyvinylphenol; polycatides; polymethacrylimide (PMI); polyalkenesulfone (PAS); polypropylene; polyethylene; polyhydroxyethylmethacrylate (HEMA); polydimethylsiloxane; polyacrylamide; polymide; and block-copolymers. Preferred supports of the present invention include silicon, silica, glass, cellulose, paper, and polymers. Supports for use in the present invention may be a combination of any of the aforementioned support materials.

In one embodiment, the support is a microarray support, such as a standard 96 well plate. The surface of the support may be flat (i.e., planar) and firm or semi-firm. Alternatively, the surface of the support need not necessarily be flat or entirely two-dimensional. Significant topological features on a planar or non-planar support may be present on the support surface. For instance, walls or other barriers may separate discrete locations on the support. Similarly, the support may have channels, wells, or discrete locations of indentations.

In other embodiments, the support has a surface coating that is optionally a metal film. Suitable metal films for protein microarrays are known and may include, without limitation, aluminum, chromium, titanium, tantalum, nickel, stainless steel, zinc, lead, iron, copper, magnesium, manganese, cadmium, tungsten, cobalt, and alloys, oxides, or mixtures thereof. In one embodiment, the metal film is a noble metal film. Noble metals that may be used for a support surface coating may include, for example, gold, platinum, silver, and/or copper. Electron-beam evaporation may be used to provide a thin coating of gold on the surface of the support. Metal films can be coated to provide the specific desired chemistry for a particular use.

Immobilization of hyaluronic acid films to solid substrates is known. See, e.g., Suh et al., "Characterization of Chemisorbed Hyaluronic Acid Directly Immobilized on Solid Substrates," *Journal of Biomedical Materials Research Part B: Applied Biomaterials* 72B(2):292-298 (2004), which is hereby incorporated by reference in its entirety. For example, high molecular weight hyaluronic acid can be directly immobilized onto both hydrophilic and hydrophobic substrates without any chemical manipulation, allowing for the formation of an ultrathin chemisorbed layer. Hyaluronic acid is stabilized on hydrophilic surfaces through hydrogen bonding between the hydrophilic moieties in HA (such as carboxylic acid (—COOH) or hydroxyl (—OH) groups) with silanol (—SiOH). Despite the water solubility, the chemisorbed hyaluronic acid layer remains stable on glass or silicon oxide substrates for at least 7 days in phosphate-buffered saline. Hyaluronic acid immobilizes on silicon and other dioxide surfaces in much higher quantities than other polysaccharides. This behavior is related to the molecular entanglement and intrinsic stiffness of hyaluronic acid as a result of strong internal and external hydrogen bonding, as well as high molecular weight. HA can also tightly adsorb onto hydrophobic surfaces, in these cases based on interactions between the hydrophobic side of the HA polysaccharide (the molecular face exposed when all the hydroxyl groups are pointing in the opposite direction) and hydrophobic constituents of the solid substrate.

Compounds other than hyaluronan may be used with the medium in carrying out the methods of the present invention. Suitable compounds may include, for example, glycoasaminoglycans, including chondroitin or chondroitin sulfate, and others.

Pursuant to the methods of the present invention, the medium comprising hyaluronan or a fragment thereof is contacted with a fluid sample from a subject with an inflammatory condition. Non-limiting examples of such fluid samples include pleural fluid samples; pulmonary or bronchial lavage fluid samples, synovial fluid samples, peritoneal fluid samples, bone marrow aspirate samples, lymph, cerebrospinal fluid, ascites fluid samples, amniotic fluid samples, sputum samples, bladder washes, semen, urine, saliva, tears, blood and its components serum and plasma, follicular fluid, ascites fluid, peritoneal dialysis fluid, and the like. The specific body fluid used for the fluid sample depends upon the particular location or type of determination being made. For example, a suitable fluid sample for carrying out the methods of the present invention, where the purpose is to predict progression of an inflammatory condition (or tailor treatment for such condition) related to a subject's knee is a synovial fluid from the knee of interest.

In the methods of the present invention, fluid samples are taken from subjects that have an inflammatory condition. Inflammatory conditions may include, but are not limited to, human inflammation, rheumatoid arthritis, rheumatoid spondylitis, osteoarthritis, asthma, gouty arthritis, sepsis, septic shock, endotoxic shock, Gram-negative sepsis, toxic shock syndrome, adult respiratory distress syndrome, stroke, reperfusion injury, neural trauma, neural ischemia, psoriasis, restenosis, chronic pulmonary inflammatory disease, bone resorptive diseases, graft-versus-host reaction, Chron's disease, ulcerative colitis, inflammatory bowel disease, pyresis, or combinations thereof.

Subjects from which fluid samples may be taken, and for which progression of an inflammatory condition is predicted or treatment of an inflammatory condition is tailored include, without limitation, humans and other primates, cats, dogs, cows, horses, pigs, sheep, and rodents such as mice and rats.

In taking and preparing a sample for use in the methods of the present invention, it may be desirable to dilute the sample in a buffer solution. Non-limiting examples of a suitable buffer solution include any in the pH range of about 6 to about 8, but a more extreme pH may also be used. Dilutions in the range from about 1:10 to at least about 1:1000 may be used, although suitable dilutions are not limited by these ranges. In carrying out the methods of the present invention, it may be necessary or desirable to lavage a body space in order to gain a sampling for measurement of inflammatory activity.

In the present invention, the fluid samples contain a protein or proteoglycan and a transfer agent. Proteins or proteoglycans of the present invention include any protein or proteoglycan that can serve as a HC donor. Particularly preferred proteins are proteins of the inter-α-inhibitor ("IαI") family. For example, one particularly preferred protein is inter-α-inhibitor, which is synonymous with inter-α-trypsin inhibitor (ITI). Another preferred protein is pre-α-inhibitor. The IαI family of proteins are a suitable source of HCs that can be transferred to hyaluronan. A particularly preferred transfer agent is TSG-6, although other transfer agents include agents capable of mediating transfer of heavy chains (HC) onto surface-bound hyaluronan. TSG-6 is a cytokine-induced gene product which, in a number of animal models of arthritis, has demonstrated inhibitory and chondroprotective effects in the presence of both acute and chronic inflammation (Bardos et al., "Anti-inflammatory and Chondroprotective Effect of TSG-6 (Tumor Necrosis Factor-alpha-stimulated Gene-6) In Murine Models of Experimental Arthritis," *Am. J. Pathol.* 159(5):1711-21 (2001); Glant et al., "Cartilage-specific Constitutive Expression of TSG-6 Protein (Product of Tumor Necrosis Factor Alpha-Stimulated Gene 6) Provides a Chondroprotective, But Not Antiinflammatory, Effect In Antigen-induced Arthritis," *Arthritis Rheum.* 46(8):2207-18 (2002); Mindrescu et al., "Up-regulation of Cyclooxygenase-2 Expression By TSG-6 Protein In Macrophage Cell Line," *Biochem. Biophys. Res. Commun.* 330(3):737-45 (2005); Mindrescu et al., "Amelioration of Collagen-induced Arthritis In DBA/1J Mice By Recombinant TSG-6, A Tumor Necrosis Factor/Interleukin-1-inducible Protein," *Arthritis Rheum.* 43(12): 2668-77 (2000); Wisniewski et al., "Cytokine-induced Gene Expression At the Crossroads of Innate Immunity, Inflammation and Fertility: TSG-6 and PTX3/TSG-14, " *Cytokine Growth Factor Rev.* 15(2-3):129-46 (2004); Mindrescu et al., "Reduced Susceptibility to Collagen-induced Arthritis in DBA/1J Mice Expressing the TSG-6 Transgene," *Arthritis Rheum.* 46:2453-64 (2002), which are hereby incorporated by reference in their entirety).

The expression of TSG-6 is induced by multiple cytokines, including, e.g., pro-inflammatory cytokines like TNF-α, IL-1, and IL-17 among others, and modulated by growth factors and hormones (gonadotropins). The determination of TSG-6 activity is, therefore, an integrated measure of multiple factors involved in inflammation and extracellular matrix metabolism. TSG-6 protein chemically modifies hyaluronan by catalyzing the transfer of protein heavy chains from IαI to hyaluronic acid, thereby generating hyaluronic acid-heavy chain ("HA-HC") products.

Figure 2:
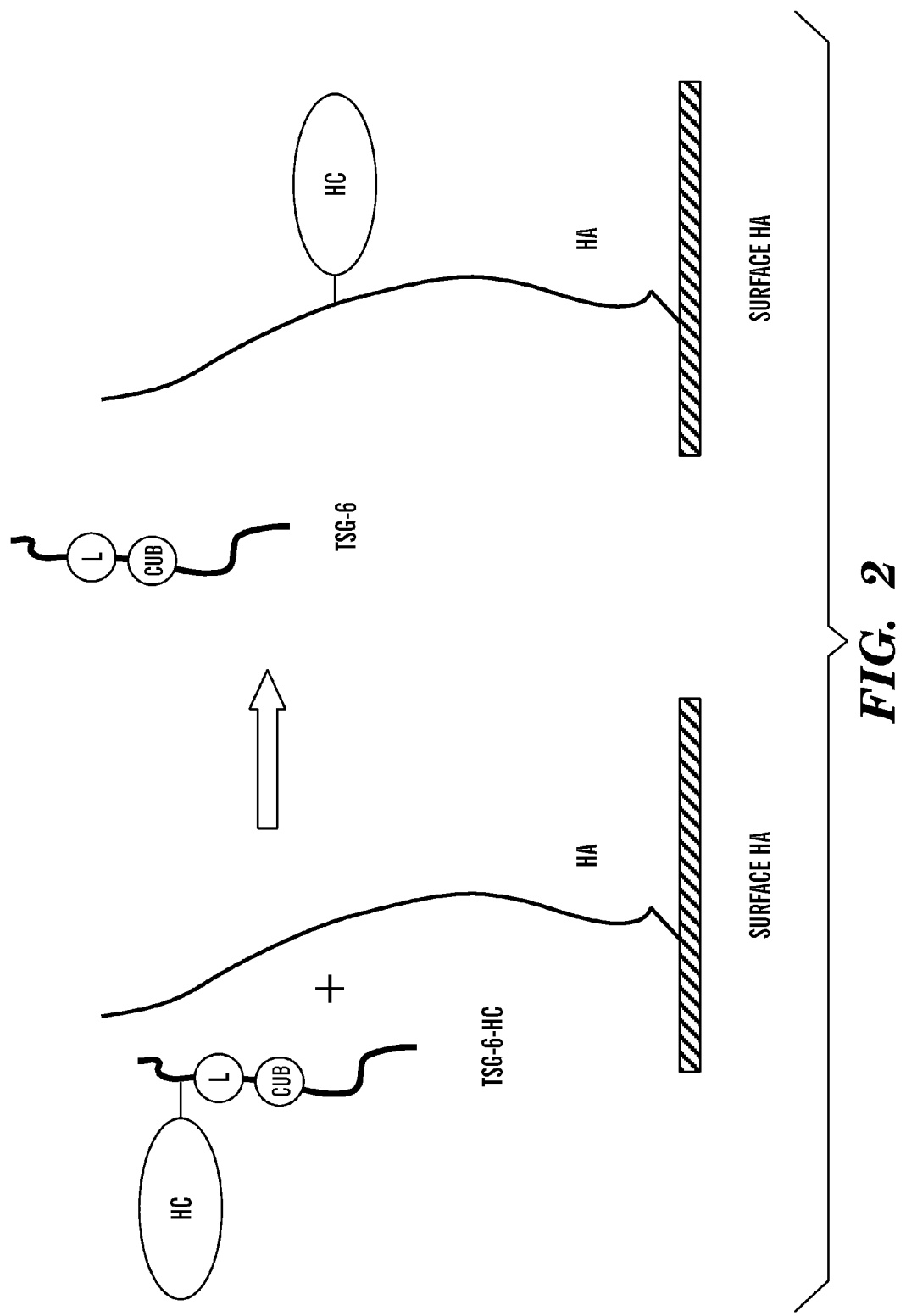
FIG. 2 is a schematic illustration of the principle of the TSG-6 activity assay according to one embodiment of the present invention, showing how in, e.g., a 96-well plate containing surface-coupled HA, HCs are transferred from TSG-6 to HA (or from IαI to HA (not shown)), resulting in surface-coupled HA-HC complexes that can be detected using the ELISA principle.

Thus, in one embodiment, the fluid sample from the subject includes IαI protein (as the heavy chain donor) and TSG-6 protein as the transfer agent. According to this embodiment, when the fluid sample is incubated with the medium, TSG-6 present in the sample mediates transfer of IαI heavy chains to the hyaluronan to form a covalent complex. One of the beneficial features of this embodiment of the present invention is that this process of TSG-6 mediated transfer of IαI heavy chains to hyaluronan can be carried out by the TSG-6 and IαI present in the fluid sample, without additional TSG-6 or IαI being added to the sample. In other words, the method is carried out under conditions where the proteins or proteoglycans (or other molecule(s)) present in the fluid sample from the subject are the only source of heavy chains in the sample, to solely determine the transfer activity measured in the sample. TSG-6 mediated HC transfer is illustrated in FIG. 1 and FIG. 2, and is further described in Sanggaard et al., "The Transfer of Heavy Chains From Bikunin Proteins to Hyaluronan Requires Both TSG-6 and HC2," *J. Biol. Chem.* 27:18530-7 (2008) and Sanggaard et al., "The TSG-6/HC-Mediated Transfer Is a Dynamic Process Shuffling HCs Between Glycosaminoglycans," *JBC* May 12, 2010, which are hereby incorporated by reference in their entirety.

In addition to TSG-6, pre-α-inhibitor, and IαI, other proteins/proteoglycans and transfer agents present in the body fluid sample may also be useful in the methods of the present invention. Suitable examples include other proteins capable of donating HCs to hyaluronan (e.g., TSG-HC complexes, or HCs attached to proteoglycans other than pre-α-inhibitor and/or IαI), and other currently unknown proteins that are capable of mediating HC transfer to hyaluronan.

The fluid sample may include diverse other biochemical species and a transfer agent capable of transferring heavy chains (HC) from the proteoglycan inter α inhibitor to hyaluronan (or other compound) in the medium, the latter believed to reflect a summation of the overall inflammatory activity in the body fluid.

In the methods of the present invention, the fluid sample is incubated with the medium (e.g., on a support) under conditions effective for the transfer agent in the fluid sample to mediate a transfer of heavy chains from the proteins or proteoglycans in the fluid sample to the hyaluronan or a fragment thereof to form a complex. These conditions may include incubation at a temperature of about 4° C. to about 60° C., or about 15-50° C., about 20-45° C., about 25-45° C., about 30-45° C., about 35-45° C., or about 37° C. Incubation times may vary, but may be as few as a few seconds to a minute and up to about 24 hours. In one embodiment, incubation is carried out for about 1-15 minutes, 15-30 minutes, 30-45 minutes, 45-60 minutes, or for about 1, 1.25, 1.5, 1.75, 2, 2.25, 2.5, 2.75, 3, 3.25, 3.5, 3.75, or 4 hours.

Occurrence levels of complexes formed during incubation pursuant to the methods of the present invention are detected using an antibody. In one embodiment, the antibodies are capable of binding to at least a portion of a heavy chain transferred from the proteins or proteoglycans to the hyaluronic acid. The antibodies can be raised against either purified complete IαI, isolated heavy chains (HC) of IαI, or HC complexes with chondroitin sulfate, oligodisaccharides of chondroitin sulfate, HC complexes with HA, or HC complexes with oligodisaccharides of HA comprising D-glucuronic acid-β1-3-N-acetyl-D-glucosamine Exemplary antibodies include, without limitation, the polyclonal rabbit anti-human inter-alpha-trypsin-inhibitor antibody (purified immunoglobulin) (an anti-HC antibody) (DakoCytomation, Glostrup, Denmark) (catalog number A 0301) and the affinity-purified polyclonal goat anti-HC antibodies sc-21970 (K-18) and sc-21975 (K-16) (Santa Cruz Biotechnology, Santa Cruz, Calif.).

Antibodies for detection may be either monoclonal antibodies or polyclonal antibodies. Monoclonal antibody production may be carried out by techniques which are well-known in the art. Basically, the process involves first obtaining immune cells (lymphocytes) from the spleen of a mammal (e.g., mouse) which has been previously immunized with the antigen of interest either in vivo or in vitro. The antibody-secreting lymphocytes are then fused with (mouse) myeloma cells or transformed cells, which are capable of replicating indefinitely in cell culture, thereby producing an immortal, immunoglobulin-secreting cell line. The resulting fused cells, or hybridomas, are cultured, and the resulting colonies screened for the production of the desired monoclonal antibodies. Colonies producing such antibodies are cloned, and grown either in vivo or in vitro to produce large quantities of antibody. A description of the theoretical basis and practical methodology of fusing such cells is set forth in Kohler et al., "Continuous Cultures of Fused Cells Secreting Antibody of Predefined Specificity," *Nature* 256:495 (1975), which is hereby incorporated by reference in its entirety.

Mammalian lymphocytes are immunized by in vivo immunization of the animal (e.g., a mouse) with the protein or polypeptide to which the antibodies are being raised. Such immunizations are repeated as necessary at intervals of up to several weeks to obtain a sufficient titer of antibodies. Following the last antigen boost, the animals are sacrificed and spleen cells removed.

Fusion with mammalian myeloma cells or other fusion partners capable of replicating indefinitely in cell culture is effected by standard and well-known techniques, for example, by using polyethylene glycol ("PEG") or other fusing agents (Milstein et al., *Eur. J. Immunol.* 6:511 (1976), which is hereby incorporated by reference in its entirety). This immortal cell line, which is preferably murine, but may also be derived from cells of other mammalian species, including but not limited to rats and humans, is selected to be deficient in enzymes necessary for the utilization of certain nutrients, to be capable of rapid growth, and to have good fusion capability. Many such cell lines are known to those skilled in the art, and others are regularly described.

Procedures for raising polyclonal antibodies are also well known. Typically, such antibodies can be raised by administering a protein or polypeptide of interest subcutaneously to New Zealand white rabbits which have first been bled to obtain pre-immune serum. The antigens can be injected at a total volume of 100 µl per site at six different sites. Each injected material will contain synthetic surfactant adjuvant pluronic polyols, or pulverized acrylamide gel containing the protein or polypeptide after SDS-polyacrylamide gel electrophoresis. The rabbits are then bled two weeks after the first injection and periodically boosted with the same antigen three times every six weeks. A sample of serum is then collected 10 days after each boost. Polyclonal antibodies are then recovered from the serum by affinity chromatography using the corresponding antigen to capture the antibody. Ultimately, the rabbits are euthanized with pentobarbital 150 mg/Kg IV. This and other procedures for raising polyclonal antibodies are disclosed in Harlow et al., eds., *Antibodies: A Laboratory Manual* (1988), which is hereby incorporated by reference in its entirety.

In addition to utilizing whole antibodies, the present invention may employ the use of binding portions of such antibodies. Such binding portions include Fab fragments, F(ab')$_2$ fragments, and Fv fragments. These antibody fragments can be made by conventional procedures, such as proteolytic fragmentation procedures, as described in Goding, *Monoclonal Antibodies: Principles and Practice*, pp. 98-118 (N.Y. Academic Press, 1983), which is hereby incorporated by reference in its entirety.

Antibodies useful in the methods of the present invention may be bound to a label. Suitable labels include, without limitation, fluorescent labels, biologically-active labels, radioactive labels, nuclear magnetic resonance active labels, luminescent labels, and chromophore labels. An antibody bound to a label is useful for diagnostic use, such as for point-of-care determination of treatment.

Assays using antibodies to detect the presence of proteins or protein complexes in a sample are well known in the art. For example, immunological detection procedures include, without limitation, enzyme-linked immunoabsorbent assay ("ELISA"), radioimmunoassay, gel diffusion precipitin reaction assay, immunodiffusion assay, agglutination assay, fluorescent immunoassay, protein A immunoassay, or immunoelectrophoresis assay.

As is appreciated by those skilled in the art, ELISAs can be performed in a number of assay formats. In one ELISA format, a host sample, e.g., a patient body fluid sample, is incubated on a solid support, e.g., the wells of a microtiter plate, or a polystyrene dish, to which hyaluronic acid is bound. Any free protein binding sites on the dish are then blocked by incubating with a non-specific protein such as bovine serum albumin. A monoclonal antibody is then added to the solid support, e.g., the wells or the dish, and allowed to incubate. During the incubation time, the monoclonal antibodies attach to any protein heavy chains that have coupled to the hyaluronic acid. All unbound monoclonal antibody is washed away using an appropriate buffer solution. The reporter antibody, e.g., linked to horseradish peroxidase, is added to the support, thereby resulting in the binding of the reporter antibody to any monoclonal antibody which has bound to the HA-HC complexes. Unattached reporter antibody is then washed away. Peroxidase substrate is added to the support and the amount of color developed in a given time period provides a measurement of the amount of protein/proteoglycan and/or transfer agent present in a given volume of patient sample when compared to a standard curve.

According to this aspect of the present invention, progression of an inflammatory condition in a subject may be predicted for about 1 month, 2 months, 3 months, 3-6 months, 6-12 months, 12-18 months, 1-2 years, 2-3 years, 3 years, 3-4 years, 4 years, 4-5 years or a 5 year period of time. Predicting progression of an inflammatory condition may involve, for example, predicting a subject's progressive radiologic change, or predicting progression toward the need for surgery at a specific location in the subject.

In carrying out the methods of the present invention, occurrence levels of the heavy chain/hyaluronan complex are compared to a reference standard to, e.g., predict progression of an inflammatory condition in a subject. According to one embodiment, a reference standard is generated by performing fluid sample tests as taught herein on subjects not suffering from an inflammatory condition. Alternatively, a reference standard is based on a purified protein (e.g., TSG-6). By these means, a baseline standard representing the absence of an inflammatory condition, or non-progression of an inflammatory condition, can be determined and/or predicted. Reference standards may also be established for individuals known to be at a particular stage of an inflammatory condition by using, e.g., reference scoring standards as described below. By this means, occurrence levels of an inflammatory condition in the subject are compared to occurrence level standards determined in individuals known to be at a particular diagnosis or stage of an inflammatory condition. Reference standards can be coordinated with time, thereby providing a reference standard that can be used to predict the progression of an inflammatory condition over time.

Thus, according to one embodiment, a fluid sample in a subject is determined to have an occurrence level of the heavy chain/hyaluronan complex and that occurrence level is compared with the reference standards to predict progression of an inflammatory condition. For example, reference scoring standards and/or progression of an inflammatory condition can be developed by scoring paired patient-knee radiographs by, e.g., blinded readers as either positive (+) or negative (−) for progressive joint space narrowing (JSN) and osteophyte (OST) formation. For example, as illustrated in Table 1, a subject's knee can definitively be classified into different OA progression groups based on the JSN/OST score and clinical profile ("−/−", "−/+", "+/+" and "TKA"). ANOVA can be applied to log-transformed values of TSG-6, and a nonparametric Kruskal-Wallis test applied to untransformed TSG-6 values. Radiographic risk groups can be compared using the Tukey pair-wise comparison procedure. Logistic regression models can be used to analyze the relationship between baseline TSG-6 levels and the different aspects of radiographic OA progression (JSN and OST), including the influence of relevant covariates. TSG-6 cut-off points to classify patients into different OA progression groups will be proposed and evaluated using Receiver Operator Characteristics (ROC) analysis.

TABLE 1

Classification of different OA progression groups.

| Group | Description |
| --- | --- |
| Non-progression | Patients whose radiograph does not change significantly between the baseline and, e.g., 3-year radiographs, (JSN−/OST−). |
| Mild radiographic progression | Patients with OST progression but no change in JSN (JSN−/OST+). |
| Rapid progression | Patients in whom both JSN and OST worsens (JSN+/OST+). |
| TKA patients | Patients in whom the study knee requires joint arthroplasty during e.g., a 3-yr observation. |

According to one embodiment, occurrence levels of the heavy chain/hyaluronan complex can be correlated to protein or proteoglycan activity. For example, occurrence levels of the heavy chain/hyaluronan complex can be correlated to, e.g., TSG-6 activity. According to this embodiment, transfer agent activity can be determined by detecting occurrence levels, and transfer agent activity can be used as a reference standard. For example, transfer agent activity (e.g., TSG-6 activity) in a sample that is at least about 2.0 fold, or at least about 2.1, 2.2, 2.3, 2.4, 2.5, 2.6, 2.7, 2.8, 2.9, or 3.0 fold, or more higher than transfer agent (e.g., TSG-6) activity in a joint that does not progress clinically or radiographically in terms of an inflammatory condition is predictive of a joint progressing to total athroplasty within a period of about three years.

In another embodiment, the reference standard is a mean transfer agent activity found in synovial fluids of healthy individuals. The mean transfer agent (e.g., TSG-6) activity may be about 3.0 nM or less, or about 1.5-4.5 nM, or about 2.0-3.5 nM, or about 2.5-3.0 nM. Equivalent synovial fluids in individuals where transfer agent (e.g., TSG-6) activity is higher than the reference standard, e.g., about 4.0, 5.0, 6.0, 7.0, 8.0, 9.0, 10.0, 11.0, 12.0, or 13.0 nM, or higher, indicates the subject has an inflammatory condition (e.g., osteoarthritis).

Another aspect of the present invention is directed to a method of tailoring treatment of an inflammatory condition in a subject in need of treatment. This method involves providing a medium comprising hyaluronan or a fragment thereof. The medium is contacted with a fluid sample from a subject with an inflammatory condition. The fluid sample comprises proteins or proteoglycans and a transfer agent. The fluid sample is incubated with the medium under conditions effective for the transfer agent in the fluid sample to mediate transfer of heavy chains from the proteins or proteoglycans to the hyaluronan or a fragment thereof to form a complex. Occurrence levels of the complex are detected using an antibody. Occurrence levels of the complex from said detecting are compared to a reference standard to predict progression of an inflammatory condition in the subject. The method further involves determining treatment of the inflammatory condition in the subject based on said comparing, thereby tailoring treatment of the inflammatory condition in the subject.

Pursuant to this aspect of the present invention, the treatment is tailored to inhibit (i) progressive joint space narrowing, (ii) osteophyte formation, or (iii) progression toward the need for total joint replacement surgery at a specific location in the subject. As used herein "inhibit" means to reduce the expected rate of progression using suitable predictive models.

Tailoring treatment of an inflammatory condition may involve prescribing, for the first time, an anti-inflammatory treatment; adding a new treatment to an already existing treatment plan, or adjusting the level of a current treatment. Alternatively, tailoring treatment may involve making a recommendation for or against joint replacement based on the detecting carried out pursuant to the method of the present invention.

In one embodiment, the methods of the present invention are point-of-care methods for predicting progression of inflammatory conditions and tailoring treatment for inflammatory conditions in a subject.

A further aspect of the present invention is directed to a method of quantifying local inflammatory activity in a body fluid. This method involves providing a medium comprising hyaluronan or a fragment thereof. The medium is contacted with a fluid sample from a subject with an inflammatory condition. The fluid sample comprises proteins or proteoglycans and a transfer agent. The fluid sample is incubated with the medium under conditions effective for the transfer agent in the fluid sample to mediate transfer of heavy chains from the proteins or proteoglycans to the hyaluronan or a fragment thereof to form a complex. Occurrence levels of the complex are detected using an antibody. Occurrence levels of the complex from said detecting are compared to a reference standard to quantify local inflammatory activity in a body fluid.

This aspect of the present invention may involve diagnosing patients for an inflammatory condition that may or may not have been known to the patient or medical professional caring for the patient based on occurrence levels of the complex detected.

In addition, this aspect of the present invention may also be utilized to monitor and/or predict the response of patients to specific treatment alternatives, e.g., the appropriate drug to use for a patient with rheumatoid arthritis, the appropriate timing for joint replacement surgery, or to predict the relative success of joint replacement surgery with different types of implants.

EXAMPLES

The following examples are provided to illustrate embodiments of the present invention but are by no means intended to limit its scope.

Example 1

Coupling of HA to Plates

HA from rooster comb or *Streptococcus pyogenes* was used. HA at a concentration of 100 µg/ml in ddH$_2$O containing sulfo-NHS at 92 µg/ml and EDC at 61.5 µg/ml was incubated in Cov-NH (100 µl/well) for 2 hours at ambient temperature and overnight at 4° C. Thereafter, the wells were washed three times with 2 M NaCl and three times with ddH$_2$O. Based on competition experiments with HA in solution, the approximate amount of HA coupled to the Covalink plates was calculated to be 8 to 9.6 µg of HA per well of Cov-HA. Thereafter, the plates were blocked with 0.5% casein in TBS pH 8.0 (TBS: 20 mM Tris pH 8.0, 500 mM NaCl) and can be stored as such for future use.

Example 2

Figure 3:
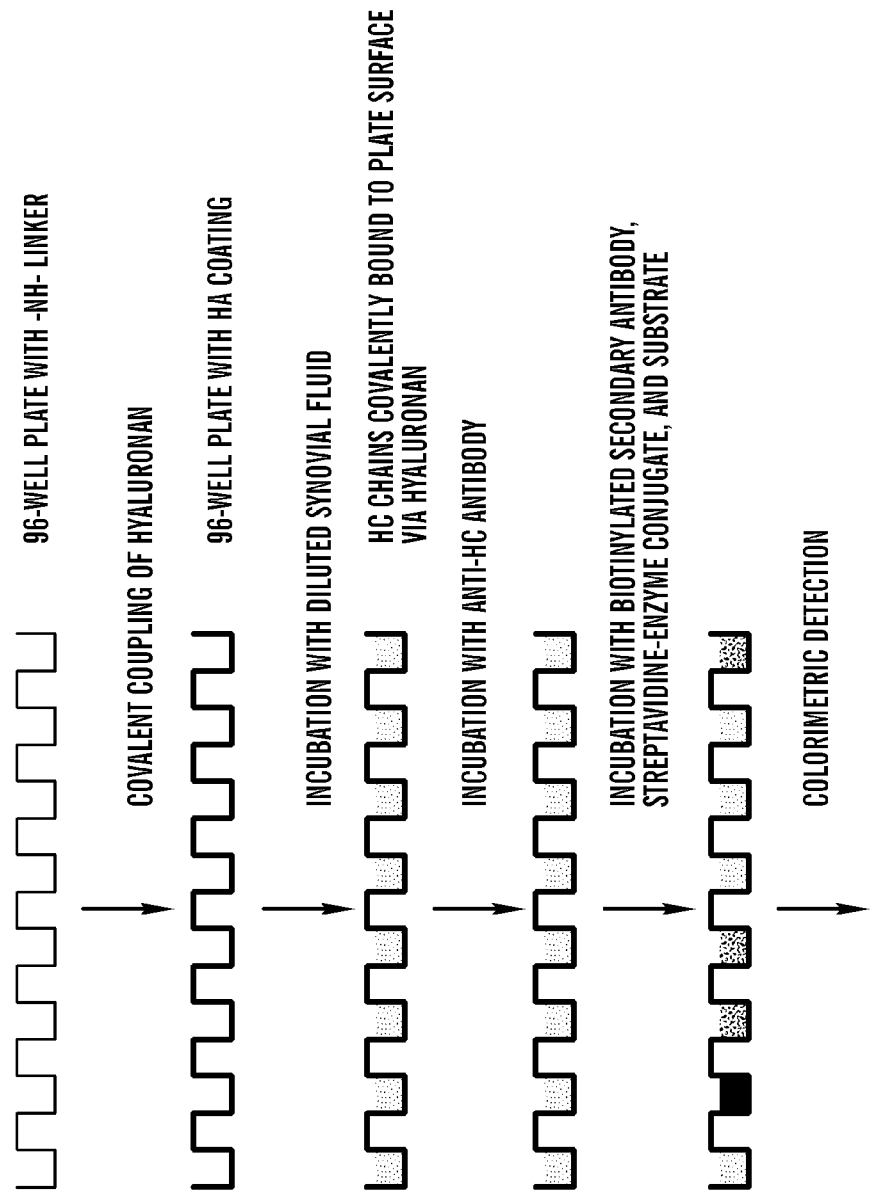
FIG. 3 is a flow diagram showing steps of a transfer activity assay according to one embodiment of the present invention. Specifically, in a 96-well plate containing surface-coupled HA, HCs are transferred from, e.g., TSG-6 to HA, resulting in surface-coupled HA-HC complexes that can be detected using the ELISA principle.
Figure 4:
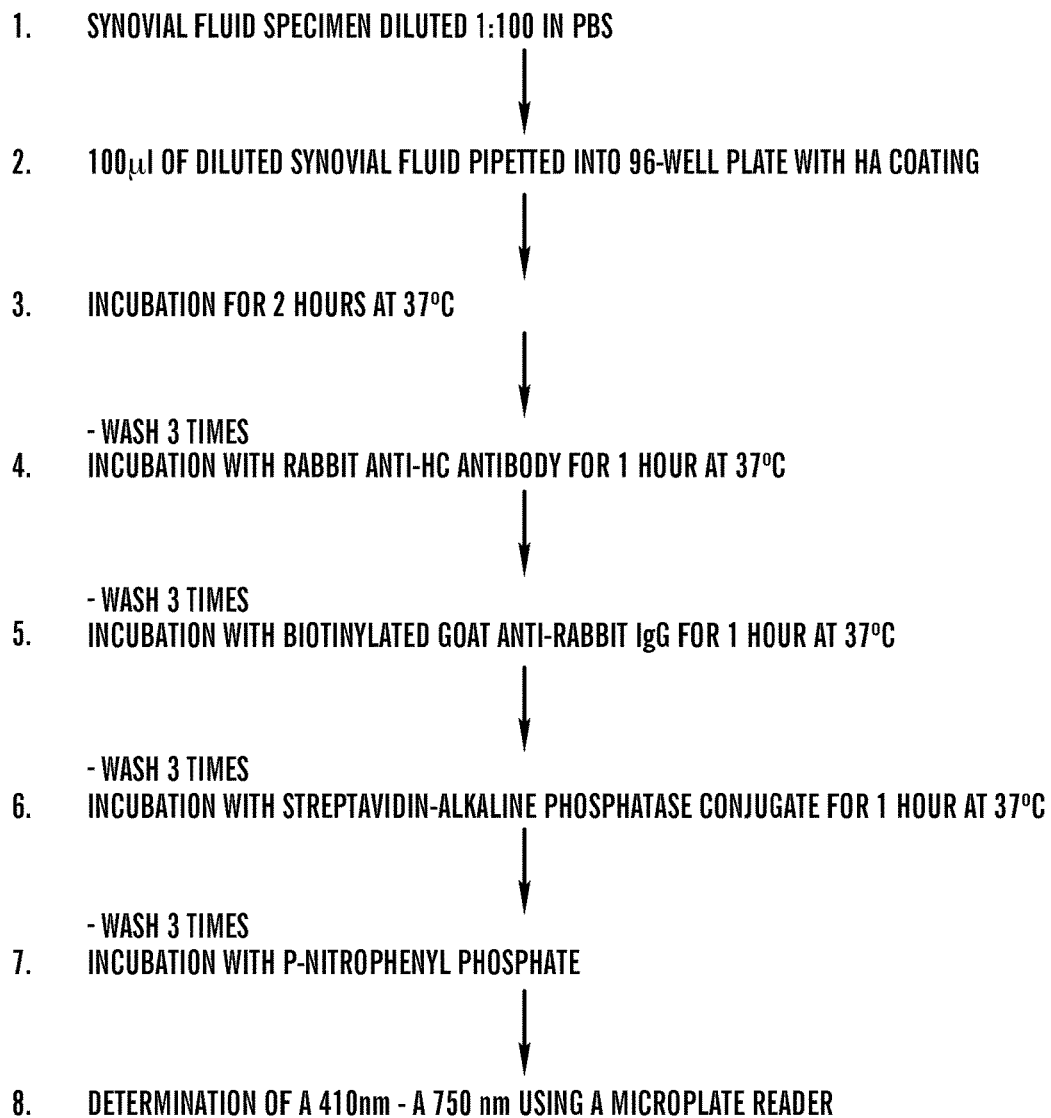
FIG. 4 is a flow diagram showing steps of a transfer activity assay according to one embodiment of the present invention. To quantify activity of a transfer agent, a standard of 1 nm recombinant transfer agent (e.g., TSG-6) is included together with a standardized source of, e.g., IαI. As a source of IαI, either purified IαI or an equivalent biological source of IαI (e.g., plasma diluted 1:1000) can be added. If plasma is used, the concentration of IαI in the plasma (ca. 3 μm) can be determined using the same assay with a known concentration of recombinant TSG-6 (e.g., 1 nM TSG-6) and suitable standards of purified IαI, or alternatively by ELISA. For all wash steps TTBS (20 mM Tris pH 7.5 containing 500 mM NaCl and 0.1% of TWEEN-20™) is used. All antibodies and the alkaline phospatase conjugate are diluted in TTBS, using dilutions between 1:1000 and 1:10000.

Data for Transfer Agent Activity Status Vs. Progression Status in Osteoarthritis Cohorts As illustrated by the flow diagrams of FIG. 3 and FIG. 4, synovial fluid samples were evaluated for TSG-6 activity using a kinetic assay. Briefly, medical grade HA (MW 2×10$^6$ DA, Lifecore) was coupled to the surface of Covalink-NH plates (Cov-NH with HA coupled to its surface is designated Covalink-HA or Cov-HA). Synovial fluid samples were diluted 1:100 in PBS and 100 µl of the diluted synovial fluid was added into one well of the Cov-HA plate. After incubation at 37° C. for 2 h, the plate was washed 3× with TTBS. Thereafter, the plate was incubated successively with rabbit anti-IαI (Dako), goat anti-rabbit, and streptavidin-alkaline phosphatase for 1 h each at 37° C. After final wash steps, the plate was incubated with the alkaline phosphatase substrate p-nitrophenyl phosphate in Tris-HCl pH 9.5 for ca. 5 min and the absorbance was determined at 410 nm, using a reference wavelength of 750 nm.

65 specimens for which data are available on OA progression were analyzed using a quantitative assay for TSG-6 activity (heavy chain (HC) transfer to hyaluronan (HA), expressed as nM TSG-6). In addition, a qualitative TSG-6 score for each synovial fluid sample was determined by Western blotting, expressed as values from 0 to 3 (0=no TSG-6 detectable, 1=weak band, 2=solid band, 3=strong band). Of the 65 specimens included in this study, 35.4% (23) were non-progressors, 40.0% (26) were OST+(JSN−), 12.3% (8) were JSN+(OST+), and 12.3% (8) had TKR. The mean TSG-6 activity in 65 synovial fluids from OA patients was 11.0 nM (SD 7.8 nM), compared to a mean TSG-6 activity in five normal synovial fluids tested of 3.0 nM (SD 1.7 nM).

Figure 5:
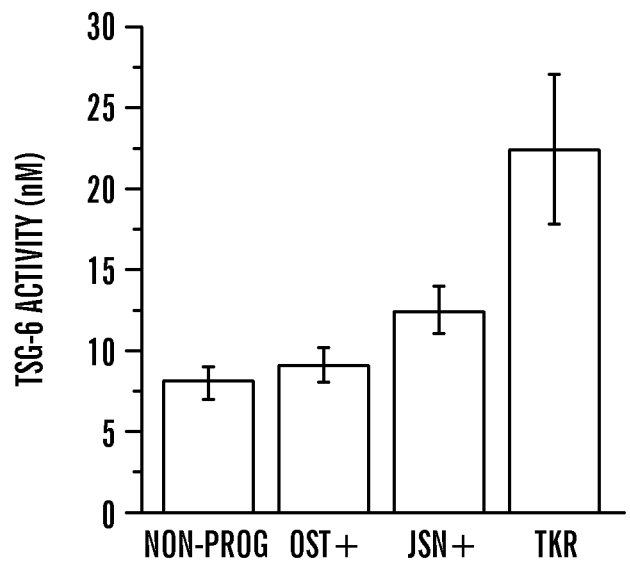
FIG. 5 is a bar graph showing mean TSG-6 activity in synovial fluids in the different outcome groups. OST+ =presence of osteophytes, JSN+=presence of joint space narrowing, TKR=total knee replacement. The bars represent the mean±SE.
Figure 6:
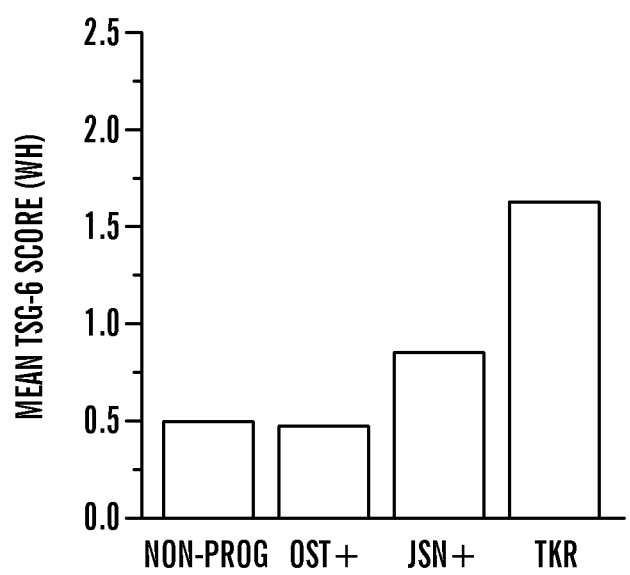
FIG. 6 is a bar graph showing mean TSG-6 scores (determined by Western blotting) of synovial fluids of different outcome groups.

FIG. 5 presents the results from a quantitative TSG-6 activity assay, based on the ability of TSG-6 to transfer heavy chains (HC) of inter-α-inhibitor (IαI) to hyaluronan (HA). The TSG-6 activity measured in a particular synovial fluid, which already contains both HC donor (IαI) and HC acceptor (HA), is not an accurate measure of the TSG-6 concentration. Instead, this assay provides a general measure of inflammatory activity in a, e.g., synovial fluid sample, as varying HA and IαI concentrations, both of which are influenced by local inflammation. Nonetheless, TSG-6 is believed to be the rate-limiting factor in the transfer reaction, and the results of this quantitative assay agree with Western blot data (FIG. 6).

Table 2 lists the mean "TSG-6 activity," expressed as a TSG-6 concentration for the different OA progression categories. TSG-6 activity cannot be strictly considered as an accurate measure of TSG-6 concentration, since inflammatory processes can influence the measured reaction rate via alteration of HA and IαI concentrations, a known consequence of inflammatory extravasation.

TABLE 2

Mean TSG-6 activity for the different OA progression categories.

| OA progression group, JSN/OST (n) | Mean TSG-6 activity, nM (SD) |
|---|---|
| No Progression (−/−) (26) | 7.75 (4.2) |
| −/+ (24) | 10.08 (5.59) |
| +/+ (7) | 11.26 (4.17) |
| TKR (8) | 23.71 (12.25) |
| −/− and −/+ (50) | 8.87 (5.01) |
| Any progression (TKR, +/+, −/+) (58) | 10.91 (8.16) |

Table 3 provides the results of a paired t-test between the group means for TSG-6 activity in different progression categories, unadjusted for multiplicity.

TABLE 3

T-test between each pair of categories.

| Comparison | p-value |
|---|---|
| TKR vs No progression (JSN/OST = −/−) | <0.01 |
| TKR vs. +/+ | <0.01 |
| TKR vs. −/+ | <0.01 |
| TKR and +/+ vs −/− and −/+ (Low Risk vs High risk) | <0.01 |
| +/+ vs. −/− | <0.1 |
| No progression vs Any progression | <0.05 |

The mean baseline TSG-6 activity in the TKR group was more than double that of the non-progressing group (Table 2). Taken together with the Western blot data, these cross-sectional analyses suggest that elevated levels of TSG-6 activity at baseline, and greater amounts of TSG-6 protein in the baseline synovial fluids, indicate an increased risk of progression to TKR over a 3-year period.

FIGS. 7A-7B provide a listing of OA patients ranked by TSG-6 activity. The mean TSG-6 activity of all specimens was 11.0±7.8 nM, while the median TSG-6 activity was 9.0 nM. Note the unequal distribution of "risk status" in this table, with low risk of progression (JSN/OST of −/− or −/+) clustered below the median, and high risk of progression (TKR or +/+) clustered above the median. The TSG-6 activity in the high versus low risk groups is also statistically significant (Table 3).

Figure 8:
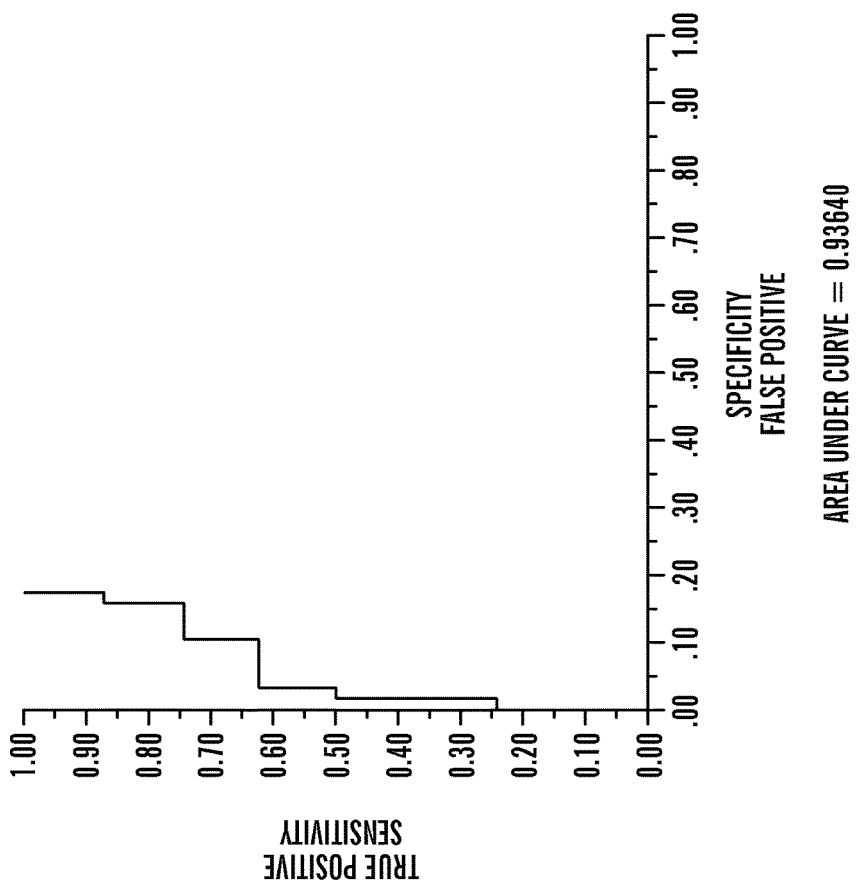
FIG. 8 is a graph showing Receiver Operator Characteristic (ROC) analysis of a transfer agent activity assay, which displays the sensitivity of the assay versus its specificity for the discrimination between patients who will have knee arthroplasty within three years (i.e., end-stage OA) versus patients who will not progress to end-stage OA. The chosen cut-off point determines sensitivity and specificity of the assay. A cut-off point maximizing the sensitivity of the assay (no false-negatives) is associated with the lowest specificity (maximal number of false-positives) and vice versa. The area under the curve is a measure of the overall performance of the assay.

As presented in FIG. 8, Receiver Operator Characteristic (ROC) analysis of the TSG-6 activity assay displays the sensitivity of the assay versus its specificity for the discrimination between patients who will have knee arthroplasty within three years (i.e., end-stage OA) versus patients who will not progress to end-stage OA. The chosen cut-off point determines sensitivity and specificity of the assay. A cut-off point maximizing the sensitivity of the assay (no false-negatives) is associated with the lowest specificity (maximal number of false-positives) and vice versa. The area under the curve is a measure of the overall performance of the assay.

Figure 9:
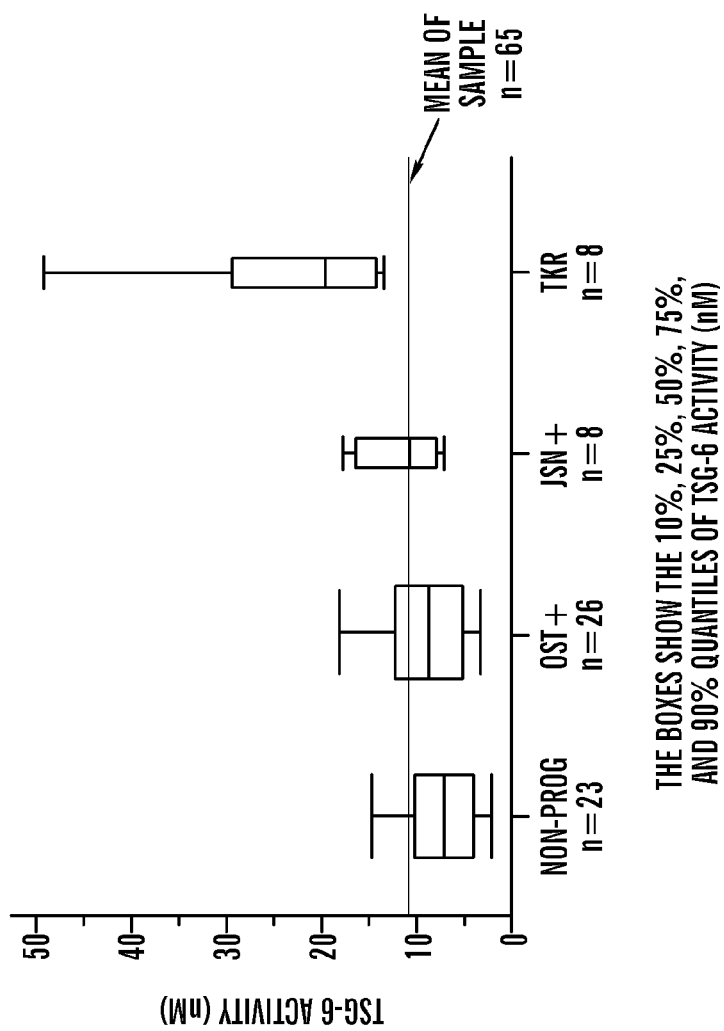
FIG. 9 is a box graph showing TSG-6 activity at baseline in the different outcome groups of OA patients in the study cohort. The outcome was determined at follow-up three years after the determination of the TSG-6 activity. Patients did either not progress (non-prog), developed osteophytes but did not exhibit joint space narrowing (OST), developed joint space narrowing (JSN, these patients also developed osteophytes), or progressed to end-stage OA requiring total knee replacement (TKR). The boxes are showing the 10, 25, 50, 75, and 90% quantiles of the TSG-6 activity in the different outcome groups.

In FIG. 9, a box graph shows TSG-6 activity at baseline in the different outcome groups of OA patients in the study cohort. The outcome was determined at follow-up three years after the determination of the TSG-6 activity. Patients did either not progress (non-prog), developed osteophytes but did not exhibit joint space narrowing (OST), developed joint space narrowing (JSN, these patients also developed osteophytes), or progressed to end-stage OA requiring total knee replacement (TKR). The boxes are showing the 10, 25, 50, 75, and 90% quantiles of the TSG-6 activity in the different outcome groups.

In the table of FIG. 10 the odds ratios for progression to end-stage OA requiring total knee replacement (TKR) or joint space narrowing (JSN) within three years after determination of the TSG-6 activity in the study cohort of OA patients is shown. An odds ratio of 1.22 for progression to TKR means that an increase of the TSG-6 activity by one unit (i.e., 1 nM) is associated with a 22% increase of the odds of progression to TKR within three years.

Figure 11:
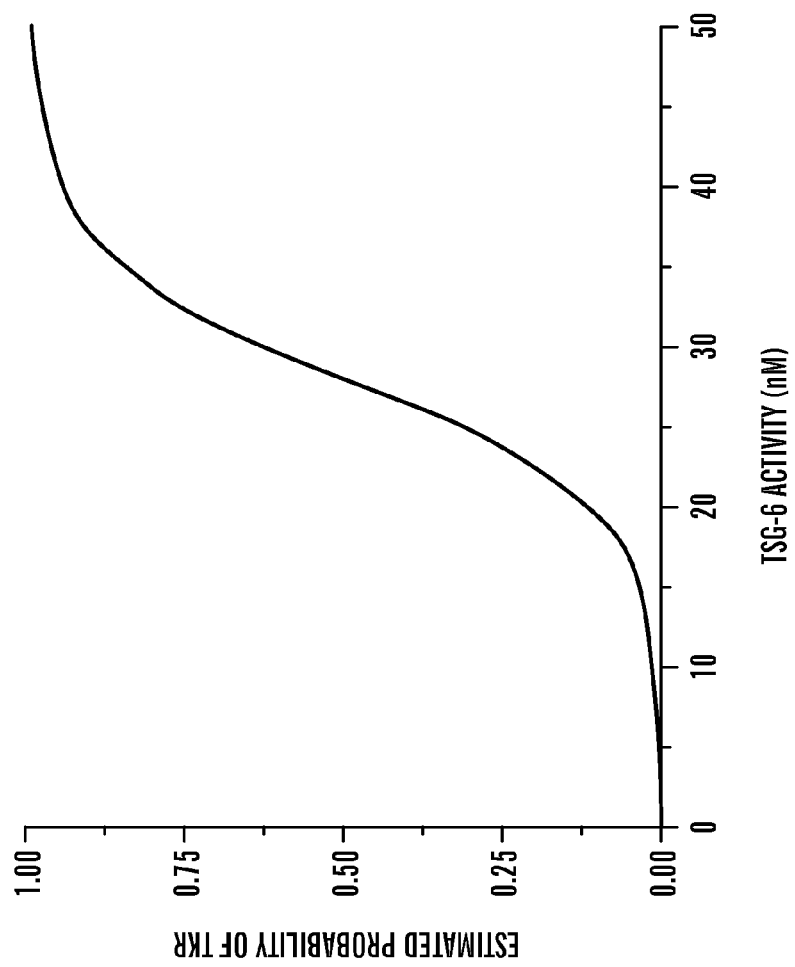
FIG. 11 is a graph showing logistic regression analysis of the TSG-6 activity for the associated probability of the alternative outcomes of either progression to end-stage OA requiring total knee replacement (TKR) versus any other outcome (including no progression, osteophyte formation, or joint space narrowing). This analysis allows estimation of the risk of any patient to progress to end-stage OA requiring arthroplasty (=probability of progression to TKR) within three years, based exclusively on the determination of the TSG-6 activity at baseline.
Figure 12:
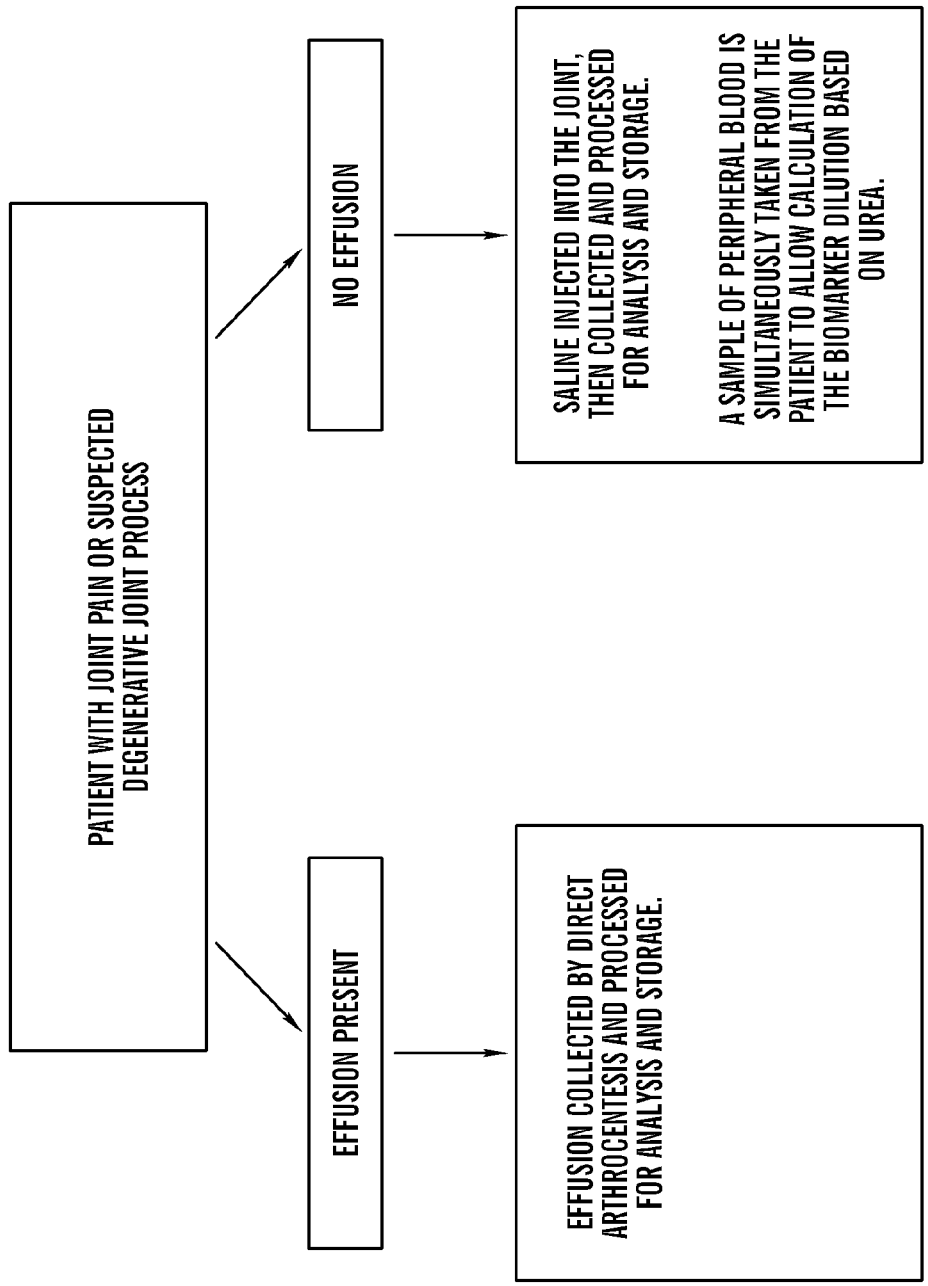
FIG. 12 is a flowchart demonstrating a procedure for obtaining tissue fluid samples for measurement of HC transfer activity using synovial fluid as an example.

Logistic regression analysis of the TSG-6 activity for the associated probability of the alternative outcomes of either progression to end-stage OA requiring total knee replacement (TKR) versus any other outcome (including no progression, osteophyte formation, or joint space narrowing) is presented in FIG. 11. This analysis allows estimation of the risk of any patient to progress to end-stage OA requiring arthroplasty (=probability of progression to TKR) within three years, based exclusively on the determination of the TSG-6 activity at baseline.

Dichotomous Definition of High and Low Risk Patients

For the purpose of correlating TSG-6 expression with the risk to progression to end stage OA, patients were grouped into either 'low risk' or 'high risk' groups (Table 4). Patients without progressive joint space narrowing (non-progressors and JSN−/OST+ patients) were categorized as 'low risk' patients and patients that either had TKA or progressed to JSN+/OST+ were categorized as 'high risk' patients. Two-sample t-tests were performed to compare log transformed TSG-6 levels for the groups. They revealed a statistically significant difference between 'low risk' and 'high risk' groups (p<0.0001). The TSG-6 activity of the high risk group was about twice the activity of the low risk group (Tables 3 and 4). These cross-sectional analyses suggest that elevated levels of TSG-6 activity at baseline indicate an increased risk of progression to TKA or worsening JSN over a 3-year period.

TABLE 4

Dichotomous Analysis of Mean TSG-6 Activity for 'High Risk' and 'Low Risk' Progression Groups.

| OA progression group, JSN/OST (n) | Mean TSG-6 activity, nM (SD) |
|---|---|
| −/− and −/+ (49) (Low Risk) | 8.8 (5.0) |
| +/+ and TKA (16) (High Risk) | 17.7 (10.8) |

TABLE 5

Paired Comparison of Combinations of Progression Groups Using Two-sample t-test on Logged TSG-6 Values Put Both Mean.

| Comparison (JSN/OST) | Estimated ratio of Median values | p-value |
|---|---|---|
| Low Risk vs High Risk | 2.01 | <.0001 |

Controlling for Covariates

Logistic regression models were used to control for covariates such as age, gender, BMI, and baseline pain measured by WOMAC pain subscale (Table 6). The logistic regression shows that there is a significant association between TSG-6 levels and TKA and JSN Progression groups when these covariates are controlled for. Specifically, every 1 unit increase in TSG-6 level is associated with a 22% increase in the odds of having TKA surgery within 3 years.

TABLE 6

Estimated odds ratios obtained from logistic regression. These values indicate the odds increase for each measure of OA progression that correspond to 1-unit increase in TSG-6 activity, and whether the relationship is statistically significant.

| Primary Outcome Measure | Odds ratio (95% CI) | p-value |
|---|---|---|
| TKA | 1.22 ([1.07, 1.41]) | 0.003* |
| OST progression (any/+) | — | 0.135† |
| OST progression without JSN progression (−/+) | — | 0.225† |
| JSN progression (+/+) | 1.23 ([1.03, 1.47]) | 0.017* |
| High Risk (+/+ and TKA) | 1.23 ([1.08, 1.40]) | 0.002* |

*Significant association with the outcome
†There was no significant association between TSG-6 and OST occurrence.

Conclusion

In summary, patients with OA have elevated TSG-6 levels in synovial fluid, and the magnitude of this elevation was found to significantly correlate to the risk of OA progression. Patients who underwent TKA had a median TSG-6 value estimated to be 2.77 times (95% CI=1.59, 4.8) higher than the non-progression group and 2.44 times higher than a mild progression group (JSN−, OST+). Dichotomous characterization of patients into a 'high risk' group (TKA or JSN+) or 'low risk' group (no radiographic progression, or only OST progression) found that high risk patients had about twice the TSG-6 activity of low risk patients. Significant association between TSG-6 levels and rapid OA progression was maintained when age, gender, BMI, and baseline pain were included as covariates in logistic regression models. These data demonstrate the potential for using synovial fluid TSG-6 activity as a measure of an individual patient's risk of OA progression. This information can be useful as patients and clinicians make important treatment decisions regarding the timing of TKA surgery, and help apply modern concepts of personalized medicine to orthopaedic decision-making.

Prophetic Example 3

Incorporating Synovial Fluid Biomarkers into Treatment Decision Algorithms for Patients with Advanced Osteoarthritis of the Knee when Little or No Effusion is Present in the Joint (So-Called "Dry Joints")

Osteoarthritis (OA) of the knee presents a current and growing challenge to available orthopaedic resources. With the anticipated increase in disease prevalence, there is a clear and pressing need to develop improved decision models with respect to the appropriate timing of TKR, and evidence-based guidelines to inform utilization of treatment alternatives. Preliminary data developed at NYU-HJD and Duke University have identified TSG-6 as a synovial fluid biomarker that is significantly associated with the risk of radiographic OA progression and the incidence of TKR.

This study will analyze whether quantitative measurements of baseline synovial fluid biomarkers, particularly TSG-6 activity, significantly predict the risk of knee OA progression to arthroplasty over a 2-year observation period. The study will additionally evaluate whether TSG-6 activity correlates with other OA biomarkers, baseline patient-reported outcome ("PRO") scores, and response to treatment alternatives commonly utilized in late stage knee OA. The objective is to develop testable hypotheses to inform patient-surgeon decision-making regarding the utilization of available treatment alternatives, and the appropriate timing of TKR.

Treatment utilization and PRO data is captured for patients with advanced OA of the knee. Inclusion and exclusion criteria are designed to enroll patients who may require an arthroplasty procedure during the subsequent 2-year period, but for whom immediate TKR is not considered medically appropriate. Each enrolled patient completes a comprehensive baseline questionnaire including systemic and musculoskeletal comorbidities, and clinical/radiographic OA history. Validated PRO instruments, the KOOS and EQ-5d, are administered at baseline and at 3-month intervals over a 2 year observation period, via Internet, e-mail, and/or telephone interviews. At the baseline visit, patients in whom no effusion is clinically detectable will be asked to consent to a small-volume closed-needle lavage procedure for synovial fluid biomarker analysis, and a small-volume blood draw that will be used to correct for dilution of synovial fluid during the lavage procedure (Kraus et al., "Urea as a Passive Transport Marker for Arthritis Biomarker Studies," *Arthritis & Rheum.* 46(2):420-427 (2002.), which is hereby incorporated by reference in its entirety). All patients will be treated per standard care for advanced knee OA, whether or not they consent to the closed-needle lavage and blood draw. Participating investigators will remain blinded to all biomarker and PRO data, so that these do not influence their current treatment decisions. The study will attempt to consent approximately 100 patients into the lavage cohort, from an anticipated 500 consecutive patients enrolling during the 6-12 month enrollment period. TSG-6 activity will be quantitated using an established method that measures the rate of heavy chain transfer to immobilized hyaluronan. Other OA markers will likewise be measured using established procedures. Clinical outcomes will be measured using PRO score changes, radiologic changes, and progression to TKR, and evaluated for their correlation to baseline biomarkers and utilization of alternative treatment strategies.

The findings of the proposed study will advance the current understanding of the natural history of knee osteoarthritis, and improve the utilization of synovial fluid biomarkers in treatment decision algorithms for patients with knee osteoarthritis. The identification of specific biomarkers capable of helping patients and surgeons understand their predicted risk of disease progression would significantly improve decision making with respect to the recommended management of symptomatic knee osteoarthritis, including the use of alternative treatments and the appropriate timing of total knee replacement.

Research Procedure

In a recent pilot study, TSG-6 (TNF-stimulated Gene 6) activity was measured in the synovial fluid of 65 patients with moderate knee OA (Kellgren and Lawrence radiographic grades 2 and 3). TSG-6 activity was found to be 2.8 times higher in knees that progressed to total knee arthroplasty ("TKA") within three years, compared to knees that did not progress clinically or radiographically (p<0.001). This relationship may support using TSG-6 as a quantitative biomarker for overall inflammatory and metabolic activity in the knee. The objective is to confirm preliminary data in this different patient cohort and use the resulting data to develop a risk profile (using logistic regression models) that can estimate an individual patient's risk for TKA based on combining TSG-6 activity and relevant covariates, providing a quantitative measure to help inform orthopaedic decision-making.

Radiographic Measurements

Weight-bearing radiographs will be obtained at baseline and at the end of the 2-year observation period using standardized knee positioning and radiographic views. Paired patient-knee radiographs will be scored by three blinded readers as either positive or negative for progressive joint space narrowing (JSN) and osteophyte (OST) formation, with each parameter scored individually. Joint space width measurements will be made for the medial and lateral compartments using the anteroposterior (AP) view, and for the patellofemoral joint using the lateral and sunrise views, utilizing the calibrated measurement function available on a digital radiograph system. A decrease in joint space of greater than 2 millimeters compared to prior radiographs will be considered positive for joint space narrowing.

For assessment of overall lower extremity alignment, each study patient will have a double stance, full length anteroposterior x-ray taken on a 51×14 inch graduated-grid cassette, which allows for visualization of both lower extremities from the hip joint to the ankle joint. For the long leg alignment radiograph, the x-ray beam is centered on the knees from a distance of 8 feet, with the patient positioned with their patellae facing forward. The mechanical axis of the entire lower limb is assessed by drawing a line from the center of the femoral head to the center of the ankle mortise, noting the relationship of this line to the center of the knee joint. Next, the anatomic axes of the patient's femur and tibia will be evaluated by drawing lines which bisect each long bone's respective medullary canal. The angle created between the anatomic axis of the femur and the anatomic axis of the tibia will be recorded and compared to the normal physiologic valgus angle of 7 degrees (+/−2 degrees) (Moreland et al., "Radiographic Analysis of the Axiel Alignment of the Lower Extremity," *J. Bone Joint Surg. Am.* 69(5): 745-749 (1987), which is hereby incorporated by reference in its entirety).

Outcome Measures

The primary outcome measure to evaluate whether TSG-6 activity is predictive of the rate of OA progression will be the incidence of scheduling the patient for TKA. Secondary outcome measures include radiologic changes scored by three blinded readers as either positive or negative for progressive joint space narrowing (JSN) and osteophyte (OST). In addition, PRO score changes from baseline will be used to evaluate the course of disease in enrolled patients from a symptomatic and quality of life perspective. It may also be used to evaluate the effectiveness of non-surgical treatments in the study population. The validated Knee Injury and Osteoarthritis Outcome Score ("KOOS") will be used to capture knee-specific outcome data. Preference-based quality of life will be quantified using the validated Euroqol instrument (EQ-5D), which can be used to calculate Quality-Adjusted Life Years. Patients who improve in their KOOS pain domain score by 40% will be considered as responders, based on this being the minimal clinically important improvement (Tubach et al., "Evaluation of Clinically Relevant Changes in Patient Reported Outcomes in Knee and Hip Osteoarthritis: The Minimal Clinically Important Improvement," *Ann. Rheum. Dis.* 64(1):29-33 (2005), which is hereby incorporated by reference in its entirety).

Prophetic Example 4

Precision and Reproducibility of the TSG-6 Activity Assay

Well-to-well variability in the TSG-6 activity assay is very low, typically below 5% for the assay conditions described. Preliminary data addressing the effect of freezing and thawing indicate that the TSG-6 activity of synovial fluids is not affected by up to five freeze-thaw cycles for both OA and RA patients. Because the synovial fluid samples used to generate the preliminary data were supplied in very limited quantities (5-10 µl), additional work will be performed using the synovial fluids obtained to investigate how the following variables affect the precision and reproducibility of the assay: repeating the assay on different days, using different batches of Cov-HA plates, and using different batches of plasma and rTSG-6 for the standard and control measurements (although a single batch of human plasma and rTSG-6 will be available for all assays in this study). Also, the question of how the number of wells used per assay affects the standard deviation of the mean and the ratio of standard deviation to mean will be analyzed. This measure of precision will be plotted against the number of wells and this information will be used to decide if a change in the number of wells used per assay is warranted. The effect of freeze-thaw cycles on TSG-6 activity analysis will be evaluated once more using these new study samples, using fresh synovial fluid specimens (never frozen) as the reference measurement. Different synovial fluid dilutions will be evaluated to determine how the dilution ratio affects the analysis, always ensuring that the TSG-6 activity in the diluted sample is below the equivalent of 1 nM TSG-6. All of these analyses will be performed using synovial fluid specimens selected because they contain sufficient volume for multiple analyses. Though the preliminary data show no indication that these factors affect the measurement results, this in-depth analysis of assay conditions will ensure the highest possible quality and reproducibility of the assay.

TSG-6 protein is expressed and purified in batches that yield 5-8 mg of purified protein. New batches are always carefully compared with a panel of previous batches for the activity of HC transfer to Cov-HA. Typically, there are no significant differences in the specific activity of different TSG-6 batches. In order to minimize the risk of minor differences in the specific activity of different TSG-6 batches, one TSG-6 batch will be designated exclusively as standard TSG-6 for all assays to be carried out within the proposed study. This will be easily possible because rTSG-6 is used as a standard at the low concentration of 1 nM. This batch of rTSG-6 will be aliquoted and stored at −80° C. for use throughout the entire study.

Although the invention has been described in detail for the purposes of illustration, it is understood that such detail is solely for that purpose, and variations can be made therein by those skilled in the art without departing from the spirit and scope of the invention which is defined by the following claims.

What is claimed:

1. A method of quantifying inflammatory activity in a joint of a subject to predict osteoarthritis progression in the joint, said method comprising:

providing a support comprising hyaluronan or a fragment thereof coupled to a surface of the support;

contacting the support with a serum sample from a subject, wherein the serum sample comprises inter-α-inhibitor protein (IαI) and TNF-stimulated gene 6 protein (TSG-6);

incubating the serum sample with the support under conditions effective for the TSG-6 in the serum sample to mediate transfer of heavy chains from the IαI to the hyaluronan or a fragment thereof to form a complex comprising a heavy chain from IαI and hyaluronan or a fragment thereof coupled to the surface of the support;

washing the support;

detecting, using an antibody, TSG-6 activity in the serum sample by determining occurrence levels of the complex coupled to the surface of the support, wherein TSG-6 activity of about 10.0 nM or higher compared to a standard of 1 nM recombinant TSG-6 indicates a quantity of inflammatory activity in the subject that may be predictive of elevated risk for progression to end stage osteoarthritis in the joint within a period of about three years.

2. The method according to claim 1, wherein the antibody is specific to heavy chains from IαI.

3. The method according to claim 1, wherein the serum sample is diluted in a buffer solution.

4. The method according to claim 1, wherein said incubating is carried out at a temperature of about 4 to about 60° C.

5. The method according to claim 1, wherein the support comprises a material selected from silicon, silica, quartz, glass, controlled pore glass, ceramic, polymer, carbon, alumina, titania, tantalum oxide, germanium, silicon nitride, zeolites, gallium arsenide, cellulose, paper, and mixtures thereof.

6. The method according to claim 1, wherein the subject is a human subject.

7. The method according to claim 1, wherein the joint is a knee joint.

8. The method according to claim 1 further comprising:

obtaining a synovial fluid sample from the joint of the subject to detect TSG-6activity in the synovial fluid sample, wherein TSG-6 activity of about 17.7 nM or higher compared to a standard of 1 nM recombinant TSG-6 is predictive of the joint progressing to total arthroplasty within a period of about three years.

* * * * *